United States Patent [19]

Salituro et al.

[11] Patent Number: 5,189,054
[45] Date of Patent: Feb. 23, 1993

[54] 3-AMIDOINDOLYL DERIVATIVES AND PHARMACEUTICAL COMPOSITIONS THEREOF

[75] Inventors: Francesco G. Salituro, Fairfield; Bruce M. Baron, Cincinnati, both of Ohio

[73] Assignee: Merrell Dow Pharmaceuticals Inc., Cincinnati, Ohio

[21] Appl. No.: 795,572

[22] Filed: Nov. 12, 1991

Related U.S. Application Data

[63] Continuation-in-part of Ser. No. 608,457, Nov. 2, 1990, abandoned.

[51] Int. Cl.⁵ .................. A61K 31/405; C07D 209/14
[52] U.S. Cl. .................................... 514/419; 548/483
[58] Field of Search ......................... 514/419; 548/483

[56] References Cited

U.S. PATENT DOCUMENTS 4,960,786 10/1990 Salituro ............................. 514/419

FOREIGN PATENT DOCUMENTS 0144986 6/1985 European Pat. Off. .
0186367 7/1986 European Pat. Off. .

OTHER PUBLICATIONS

Monge et al., *J. Heterocyclic Chemistry*, 24, pp. 437–439 (1987).
Bailey, et al., *J. C. S. Perkin I*, pp. 1602–1606, (1973).
J. T. Greenamyre, "The Role of Glutamate in Neurotransmission and in Neurologic Disease," Arch Neurol, vol. 43, pp. 1058–1063 (1986).
J. W. Olney, "Excitatory Amino Acids and Neuropsychiatric Disorders," Biol Psychiatry 26, pp. 505-525 (1989).
M. B. Robinson et al., "Glutamate and Related Acidic Excitatory Neurotransmitters: from Basic Science to Clinical Application," FASEB J. 1:446–455 (1987).
R. Dingledine et al., "Excitatory Amino Acid Receptors in Epilepsy," TiPS vol. 11, pp. 334–338 (1990).

*Primary Examiner*—Mary C. Lee
*Assistant Examiner*—Jacqueline Haley
*Attorney, Agent, or Firm*—J. Michael Dixon

[57] ABSTRACT

The present invention is directed to a new class of 3-amido and 3-sulfamido-indolyl NMDA antagonists and their use in the treatment of a number of disease states.

74 Claims, No Drawings

3-AMIDOINDOLYL DERIVATIVES AND PHARMACEUTICAL COMPOSITIONS THEREOF

This is a continuation in part of application Ser. No. 07/608,457, filed Nov. 2, 1990 now abandoned.

The present invention is directed to a new class of 3-amido and 3-sulfamido-indolyl derivatives that are useful as NMDA antagonists. Another aspect of the invention is directed to their use in the treatment of a number of diseases as well as to pharmaceutical compositions containing them.

In accordance with the present invention, a new class of NMDA antagonists have been discovered which can be described by the following formulae:

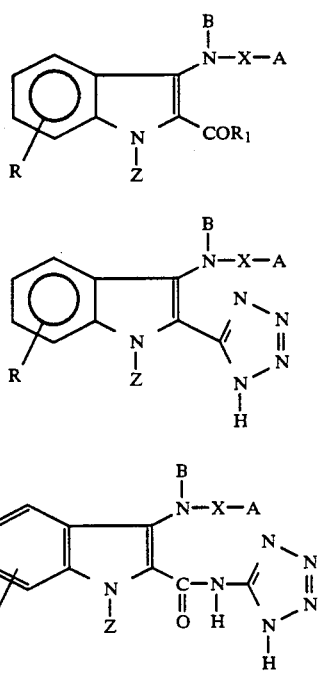

in which Z is represented by h, $C_1$-$C_4$ alkyl, phenyl, substituted phenyl, or an phenylalkyl substituent in which the phenyl ring may be optionally substituted; R is represented by hydrogen, halogen, $C_1$-$C_4$ alkyl, $C_1$-$C_4$ alkoxy, $CF_3$, $OCF_3$, OH, $NO_2$, or CN; B is represented by hydrogen, $C_1$-$C_4$ alkyl, optionally substituted phenylalkyl, or —$CH_2$—$COR_2$; X is represented by CO or $SO_2$; A is represented by a substituent selected from the group consisting of:

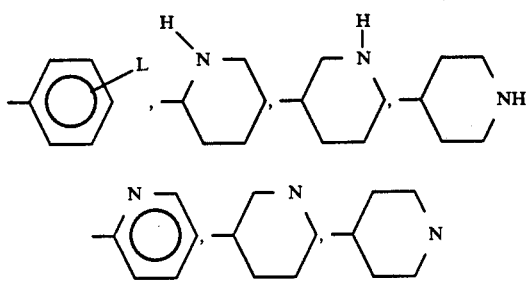

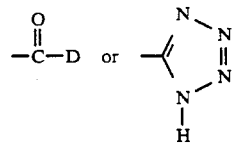

in which L is represented by a substituent selected from the group consisting of hydrogen, halogen, $C_1$-$C_4$ alkyl, $C_1$-$C_4$ alkoxy, $CF_3$, $OCF_3$, OH, $NO_2$, $NH_2$, phenylalkyl, acetyloxy, or CN; $R_1$, $R_2$, and D are each independently represented by a substituent selected from the group consisting of —OH, —$OR_3$, —$NR_4R_5$, —$OCH_2OR_3$, and —O—$(CH_2)_m$—$NR_6R_7$, in which m is an integer from 1–4; $R_3$ is represented by $C_1$-$C_4$ alkyl, phenyl, substituted phenyl or an phenylalkyl substituent in which the phenyl ring may be optionally substituted; $R_4$ and $R_5$ are each independently represented by hydrogen or a $C_1$-$C_4$ alkyl; $R_6$ and $R_7$ are each independently represented by hydrogen or a $C_1$-$C_4$ alkyl, or $R_6$ and $R_7$ together with the adjacent nitrogen atom form a piperidino, morpholino, or pyrrolidino group; the pharmaceuticaly acceptable salt thereof; with the following proviso's 1) that when R, Z, B, are hydrogen, $R_1$ is $OR_3$ in which $R_3$ is ethyl, and X is CO, then L is not hydrogen; 2) that when X is $SO_2$, R and B are hydrogen, and Z is methyl, then L is not para $NO_2$ or para Methyl; 3) that when X is $SO_2$, R and B are hydrogen, and Z is H, then L is not para Cl; 4) that when X is $SO_2$, A cannot be C(O)—D or tetrazole.

As used in this application:

a) the term "halogen" refers to a fluorine, chlorine, or bromine atom;

b) the terms "lower alkyl group and $C_{1-4}$ alkyl" refer to a branched or straight chained alkyl group containing from 1–4 carbon atoms, such as methyl, ethyl, n-propyl, isopropyl, n-butyl, isobutyl, etc.;

c) the terms "lower alkoxy group and $C_{1-4}$ alkoxy" refer to a straight or branched alkoxy group containing from 1–4 carbon atoms, such as methoxy, ethoxy, n-propoxy, isopropoxy, n-butoxy, isobutoxy, etc.;

d) the term "substituted phenyl ring" refers to a phenyl moiety ($C_6H_5$) which is substituted with up to 3 substituents, each substituent is independently selected from the group consisting of halogens, $C_{1-4}$ alkyl, $C_{1-4}$ alkoxy, $CF_3$, $OCF_3$, OH, CN, $NH_2$ and $NO_2$. These substituents may be the same or different and may be located at any of the ortho, meta, or para positions.

e) the term "phenylalkyl substituent" refers to the following structure, —$(CH_2)_p$—$C_6H_5$, in which p is an integer from 1–3. This phenyl ring may be substituted in the manner described immediately above unless substitution is expressly excluded.

f) the term "unsubstituted alkylphenyl substituent" refers to the following structure, —$(CH_2)_p$—$C_6H_5$, in which p is an integer from 1–3.

f) the expression pharmaceutically acceptable additions salts thereof refers to either acid addition salts or to basic additions salts;

g) the term carbonyl refers to: CO, h) the term sulfoxide refers to: $SO_2$, and;

i) the term tetrazole refers to:

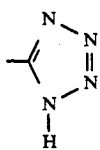

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form.

The indole ring depicted in Formulae Ia-c is always substituted at positions 2 and 3, and may be optionally substituted at position 1. It may be further substituted as is indicated by the possible definitions for R. R may represent up to 3 additional substituents and these additional substituents may be located at any of positions 4, 5, 6, or 7. These substituents can be the same or different. X may be represented by either C(0) or $SO_2$. If X is $SO_2$, then A should not be C(O)—D or tetrazole.

$R_1$, $R_2$, and D may contain either a phenyl or a phenylalkyl substituent in which the phenyl ring may be optionally substituted. There may be up to 3 substituents occuring on these phenyl rings and these substituents may be located at any of the ortho, meta, or para positions. The specific substitutions may be any of those listed above in the definition of substituted phenyl ring. Z may also, be represented either by a substituted phenyl ring or a phenylalkyl substituent in which the phenyl ring may be substituted. These phenyl rings may also contain up to 3 substituents which may be located at any of the ortho, meta, or para positions. The specific substitutions may be any of those listed above in the definition of substituted phenyl ring.

$R_1$, $R_2$, and D may be represented by the same substituent or differing substituents. Likewise $R_4$ and $R_5$ may be represented by the same substituent or differing substituents. When $R_6$ and $R_7$ are represented by hydrogen or a $C_{1-4}$ alkyl, they may represent the same or differing substituents. When $R_6$ and $R_7$ form a hetrocyclic ring along with the indicated nitrogen atom, the nitrogen atom of the hetrocycle is always bonded to the adjacent alkylene group.

It is preferred for the indolyl ring to be substituted, more preferably for the substitution to occur at positions 4 and 6, 5 and 6, or 6. It is also prefered that these substituents be halogen atoms such as chlorine atoms. It is preferred for B to be a non-hydrogen substituent and for A to be phenyl.

Examples of compounds encompassed by the present invention include:

1) 3-[(2-hydroxyphenacyl)amino]-2-carboxy-6-chloroindole;
2) 3-[(phenacyl)amino]-2-carboxy-6-chloroindole;
3) 3-[(phenacyl)amino]-2-[(2-dimethylamino)carbethoxy]-6-chloroindole;
4) 3-[(phenacyl)amino]-2-carbethoxy-6-chloroindole;
5) 3-[(2-acetoxyphenacyl)amino]-2-carbethoxy-6-chloroindole;
6) 3-[(oxalyl)amino]-2-carboxy-6-chloroindole;
7) 3-[(methyloxalylate)amino]-2-carbmethoxy-6-chloroindole;
8) 3-[(phenacyl)methylamino]-2-carboxy-4,6-dichloroindole;
9) 3-[(phenacyl)amino]-2-carboxy-4,6-dichloroindole;
10) 3-[(oxalyl)amino]-2-carboxy-4,6-dichloroindole;
11) 3-[(3-pyridacyl)methylamino]-2-carboxy-4,6-dichloroindole;
12) 3-[(3-pyridacyl)methylamino]-2-carbethoxy-4,6-dichloroindole;
13) 3-[(3-pyridacyl)amino]-2-carbethoxy-4,6-dichloroindole;
14) 3-[(3-pyridacyl)amino]-2-carboxy-4,6-dichloroindole;
15) 3-[(phenacyl)methylamino]-2-[(2-dimethylamino)-carbethoxy]-4,6-dichloroindole;
16) 3-[(phenacyl)methylamino]-2-carbethoxy-4,6-dichloroindole;
17) 3-[(phenacyl)amino]-2-carbethoxy-4,6-dichloroindole;
18) 3-[(methyloxalylate)amino]-2-carbethoxy-4,6-dichloroindole;
19) 3-[(2-benzylphenacyl)amino]-2-carbethoxy-4,6-dichloroindole;
20) 3-[(2-benzylphenacyl)amino]-2-carboxy-4,6-dichloroindole;
21) 3-[(2-benzylphenacyl)methylamino]-2-carbethoxy-4,6-dichloroindole;
22) 3-[(2-benzylphenacyl)methylamino]-2-carboxy-4,6-dichloroindole;
23) 3-[(phenylsulfonyl)amino]-2-carbethoxy-4,6-dichloroindole;
24) 3-[(phenylsulfonyl)amino]-2-carboxy-4,6-dichloroindole;
25) 3-[(phenacyl)ethylamino]-2-carbethoxy-4,6-dichloroindole;
26) 3-[(phenacyl)ethylamino]-2-carboxy-4,6-dichloroindole;
27) 3-[(phenacyl)benzylamino]-2-carbethoxy-4,6-dichloroindole;
28) 3-[(phenacyl)carbethoxymethyl-amino]-2-carbethoxy-4,6-dichloroindole;
29) 3-[(phenacyl)benzylamino]-2-carboxy-4,6-dichloroindole;
30) 3-[(phenacyl)carboxymethyl-amino]-2-carboxy-4,6-dichloroindole;
31) 3-[(phenylsulfonyl)methylamino]-2-carbethoxy-4,6-dichloroindole;

32) 3-[(phenylsulfonyl)methylamino]-2-carboxy-4,6-dichloroindole;
33) 3-[(4-nitrophenacyl)amino]-2-carbethoxy-4,6-dichloroindole;
34) 3-[(4-aminophenacyl)amino]-2-carbethoxy-4,6-dichloroindole;
35) 3-[(methyloxalylate)benzylamino]-2-carbethoxy-4,6-dichloroindole;
36) 3-[(methyloxalylate)methylamino]-2-carbethoxy-4,6-dichloroindole;
37) 3-[(4-nitrophenacyl)amino]-2-carboxy-4,6-dichloroindole;
38) 3-[(oxalyl)benzylamino]-2-carboxy-4,6-dichloroindole;
39) 3-[(oxalyl)methylamino]-2-carboxy-4,6-dichloroindole.

A general synthetic procedure for the preparation of compounds of Formula Ia is set forth in Scheme Ia. In Scheme I, all substituents, unless otherwise indicated, are as previously defined.

In general, an appropriate 3-amidoindolyl derivative of Formula Ia can be prepared in a multi-step process.

In Scheme I, the 2-aminobenzonitrile derivative as described by structure (1) is obtained commercially or prepared from the appropriately substituted 2-nitrobenzoic acid by one of ordinary skill in the art. For example, the appropriate 2-nitrobenzoic acid derivative can be converted to the acid chloride with a chlorinating reagent such as thionyl chloride and then coupled with tert-butylamine to provide the appropriately substituted amide. The nitro functionality is then reduced by reacting the derivative dissolved in a protic solvent such as ethanol with hydrogen in the presence of a catalyst such as palladium on carbon. The resulting aniline derivative is then dehydrated by treatment with trifluoroacetic anhydride in an organic solvent such as methylene chloride at room temperature to afford the appropriately substituted 2-aminobenzonitrile of structure (1) as the N-trifluoroacetate which is used directly in step a of Scheme I.

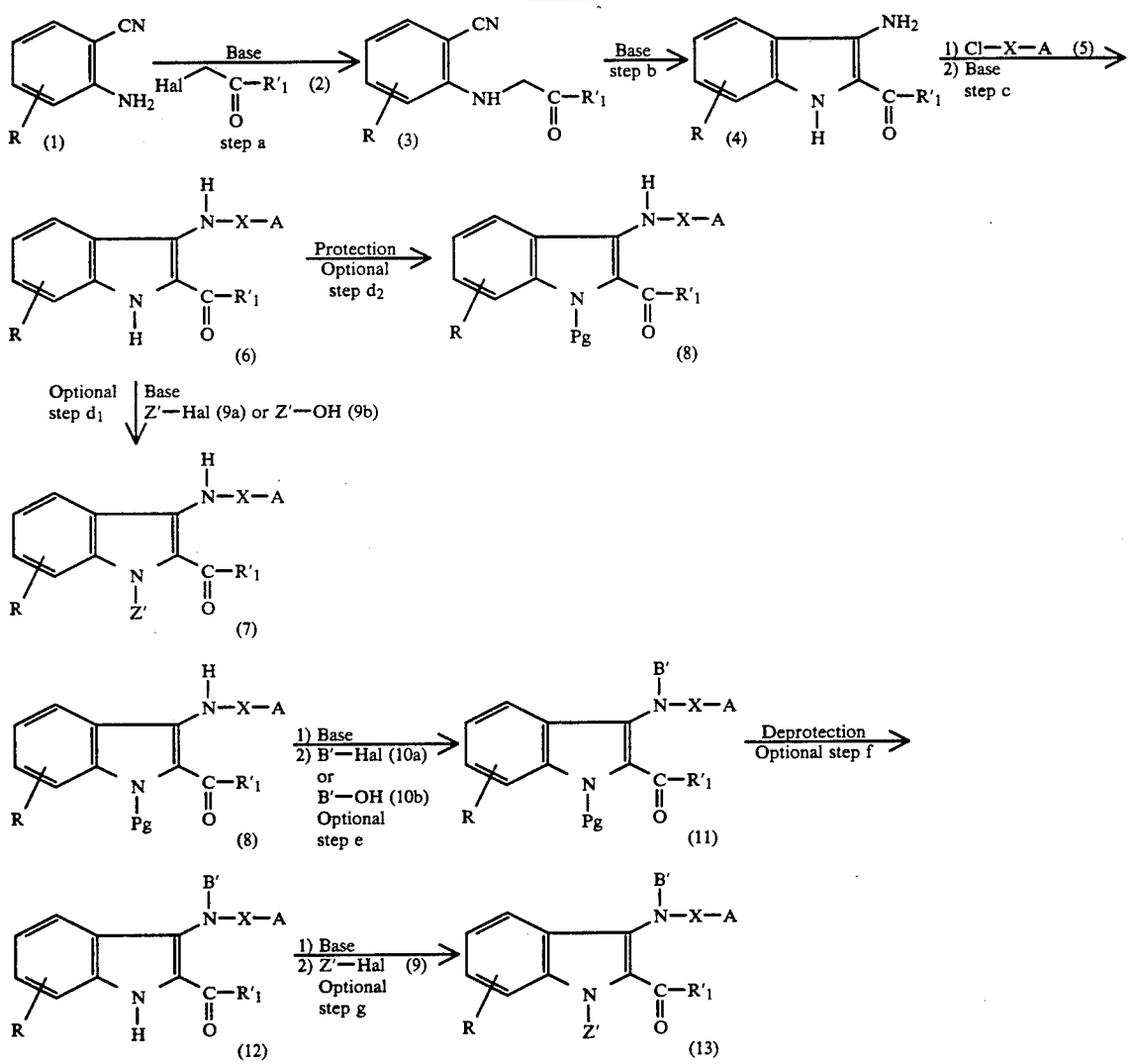

Scheme I $R'_1 = OR_3$
$B' = C_1$-$C_4$ alkyl, $-CH_2-COR_2$, or alkylphenyl
$Z' = C_1$-$C_4$ alkyl or alkylphenyl, phenyl or substituted phenyl
Hal = Cl or Br The appropriately substituted 2-aminobenzonitrile as described by structure (1) in Scheme I can be prepared using another method by one of ordinary skill in the art. For example, the appropriate 2-aminobenzoic acid derivative can be converted to the succinimide ester by treatment with triphenylphosphine, diethyl azodicarboxylate and N-hydroxy succinimide in an organic solvent such as tetrahydrofuran to provide the succinimide ester. This is then treated with tert-butylamine at room temperature in an organic solvent such as tetrahydrofuran to provide the N-tertbutylamide derivative. This compound is dehydrated with trifluoroacetic anhydride in an organic solvent such as methylene chloride at room temperture to afford the appropriately substituted 2-aminobenzonitrile of structure (1) as the N-trifluoroacetate which is used dirctly in step a of Scheme I.

Step a of Reaction Scheme I, a 2-aminobenzonitrile derivative as described by structure (1) is subjected to an alkylation reaction with an alkyl haloacetate derivative as described by structure (2) to produce an alkyl 2-anilinoacetate derivative as described by structure (3).

The alkylation reaction of Step a can be carried out using techniques known in the art. Typically, the 2-aminobenzonitrile derivative described by structure (1) is contacted with a molar excess of an alkyl haloacetate derivative as described by structure (2) and a molar excess of a base, such as potassium carbonate. The reactants are typically contacted in an organic solvent such as dimethylformamide. The reactants are typically stirred together for a period of time from about 24 hours to 6 days at a temperature range of from room temperature to reflux. The anilinoacetate derivative as described by structure (3) can be recovered from the reaction by techniques such as flash chromatography. It can then be optionally purified by recrystallization from a solvent such as hexane.

In Step b of Reaction Scheme I, an alkyl 2-anilinoacetate derivative as described by structure (3) is cyclized with an appropriate non-nucleophilic base, such as potassium tert-butoxide, to produce a 2-carbalkoxy-3-amino indole as described by structure (4).

The cyclization reaction of Step b can also be carried out using techniques known in the art. Typically, the alkyl 2-anilinoacetate derivative as described by structure (3) is contacted with an equimolar amount of a base, such as potassium tert-butoxide. The reactants are typically contacted in an anhydrous organic solvent such as tetrahydrofuran. The reactants are typically stirred together for a period of time from about 3 hours to 24 hours at a temperature range of about 0° C. to room temperature. The 2-carbalkoxy-3-amino indole as described by structure (4) can be recovered from the reaction by techniques such as flash chromatography. It can then be optionally purified by recrystallization from a solvent system such as hexane/ethyl acetate.

In Step c of Reaction Scheme I, the amino functionality of a 2-carbalkoxy-3-amino indole as described by structure (4) is subjected to an acylation reaction with an appropriate acid chloride or sulfonyl chloride as described by structure (5) to produce a 3-amidoindolyl derivative as described by structure (6).

The acylation reaction of step c can also be carried out using techniques known in the art. Typically, the 2-carbalkoxy-3-amino indole as described by structure (4) is contacted with a molar excess of an acid chloride or sulfonyl chloride and a molar excess of a base, such as triethylamine. The reactants are typically contacted in an anhydrous organic solvent, such as tetrahydrofuran or methylene chloride. The reactants are typically stirred together for a period of time ranging from 5 minutes to 24 hours and at a temperature range of from room temperature to reflux. The 3-amidoindolyl derivative as described by structure (6) can be recovered from the reaction by techniques such as recrystallization from a solvent system such as hexane/ethyl acetate.

In addition, the 3-amidoindolyl derivative as described by structure (6) can be further fuctionalized as described by Optional Steps d-g in Reaction Scheme I.

For example, in Optional Step $d_1$, the indole nitrogen functionality of the 3-amidoindolyl derivative as described by structure (6) can be subjected to an alkylation reaction to produce a 3-amido-1-alkylindolyl derivative as described by structure (7).

One method for carrying out the alkylation reaction of optional step $d_1$ can be carried out using techniques known in the art. Typically, the 3-amidoindolyl derivative as described by structure (6) is first contacted with a molar excess of a base, such as sodium hydride. The reactants are typically contacted in an anhydrous organic solvent, such as tetrahydrofuran or dimethylformamide. The reactants are typically stirred together for a period of time ranging from 15 minutes to 5 hours and at a temperature range of from 0° C. to room temperature.

A molar excess of an alkyl halide derivative as described by structure (9a) is then added and the reactants are stirred together for a period of time ranging from 2 hours to 24 hours and at a temperature range of from $-10°$ C. to room temperature. The 3-amido-1-alkylindolyl derivative as described by structure (7) is recovered from the reaction by techniques such as flash chromatography. It can then be optionally purified by recrystallization from a solvent system such as ethyl acetate/hexane.

Another suitable alkylation method is to contact a compound as described by structure (6) with a molar excess of triphenylphosphene, a molar excess of diethylazodicarboxylate, and an appropriate alcohol derivative as described by structure (9b). The reactants are typically contacted in an anhydrous organic solvent, such as tetrahydrofuran. The reactants are typically stirred together for a period of time ranging from 1 hour to 24 hours and at a temperature range of from 0° C. to room temperature. The 3-amido-1-alkylindolyl derivative as described by structure (7) is recovered from the reaction by techniques such as flash chromatography. It can then be optionally purified by recrystallization from a solvent system such as ethyl acetate/hexane.

In Optional Step $d_2$, the indole nitrogen functionality of the 3-amidoindolyl derivative as described by structure (6) can be protected by a suitable protecting group, such as tert-butyloxycarbonyl, to allow further functionalization.

The protection step of optional step $d_2$ can also be carried out using techniques known in the art. Typically, the 3-amidoindolyl derivative as described by structure (6) is contacted with an equimolar amount of di-tert-butyl dicarbonate and a catalytic amount of a base, such as dimethylaminopyridine. The reactants are typically contacted in an organic solvent, such as tetrahydrofuran. The reactants are typically stirred together for a period of time ranging from 1 hour to 24 hours at a temperature range of from room temperature to reflux. The protected 3-aminoindolyl derivative as described by structure (8) can be recovered from the reaction by techniques such as flash chromatography. It can then by optionally purified by recrystallization from a solvent system such as ethyl acetate/hexane.

In Optional Step e, the 3-amido functionality of the suitably protected 3-amidoindolyl derivative as described by structure (7) can be subjected to an alkylation reaction to produce a 3-amidoindolyl derivative as described by structure (11). Reactants and reaction conditions are typically as described previously in optional step $d_1$.

In Optional Step f, the indole nitrogen protecting group functionality of the 3-amidoindolyl derivative as described by structure (11) can be removed under acidic conditions to produce a 3-N-alkylamidoindolyl derivative as described by structure (12).

The deprotection reaction of optional step f can also be carried out using techniques well known in the art. Typically, the protected 3-amidoindolyl derivative described by structure (11) is contacted with a molar excess of an acid, such as trifluoroacetic acid. The reactants are typically contacted in an organic solvent, such as methylene chloride. The reactants are typically stirred together for a period of time ranging from 1 hour to 24 hours at a temperature range of 0° C. to reflux. The 3-N-alkylamidoindolyl derivative as described by structure (12) can be recovered from the reaction by techniques such as flash chromatography. It can then be optionally purified by recrystallization from a solvent system such as ethyl acetate/hexane.

In Optional Step g, the indole nitrogen functionality of the 3-N-alkylamidoindolyl derivative as described by structure (12) can be subjected to an alkylation reaction to produce a 3-amidoindolyl derivative as described by structure (13). Typically, the reactants and reaction procedures are as described previously in optional step $d_1$.

In addition, those 3-amidoindolyl compounds of structures (6), (7), (12), and (13) in which either $R_1$ and/or $R_2$ are represented by $-OC_1-C_4$, can be further functionalized by either a deprotection reaction and/or an additional functionalization reaction.

The deprotection reaction can be carried out using hydrolytic techniques known per se. Typically, the protected 3-amidoindolyl derivative as described by structures (6), (7), (12), or (13), in which either $R_1$ and/or $R_2$ are represented by $-OC_1-C_4$, is subjected to a basic hydrolysis. The compound is contacted with a 2 to 3 molar excess of an inorganic base such as lithium hydroxide. The hydrolysis is carried out at a temperature range of from about 25° C. to about 50° C. for a period of time ranging from 1 to 5 hours. The desired compound of Formula Ia can then be recovered from the reaction zone by flash chromatography and optionally purified by recrystallization from a solvent system such as ethyl acetate/hexane.

The various ester and amide derivatives encompassed by Formula Ia can be prepared by techniques known in the art. One method of preparing the amide derivatives is to contact a compound of Formula Ia, in which either $R_1$ and/or $R_2$ is represented by $-OH$, with a halogenating agent such as thionyl chloride, oxalyl chloride, phosphorus oxychloride, phosphorus pentachloride, etc. The resulting mono or diacid halides is then contacted with an excess of an amine represented by $-HNR_3R_4$, in which $R_3$ and $R_4$ are as previously defined. In a similar fashion, the ester derivatives can be prepared by contacting the mono or diacid halides with an excess of an alcohol represented by $HOC_1-C_4$.

Another suitable esterification method is to contact a compound of Formula Ia, in which either $R_1$ and/or $R_2$ are represented by OH, with a base, such as diethylisopropylamine, in a polar inert solvent, such as dimethylformamide, dimethylsulfoxide, acetonitrile, acetone or tetrahydrofuran, thereby forming a mono or bis carboxylate salt. The mono or bis carboxylate salt is then contacted with 2 to 5 equivalents, preferable about 2.5 equivalents, of an alkylhalide corresponding to the desired ester, and allowed to react at a temperature of about 25° C. for a period of time ranging from 16–24 hours. The reaction mixture is then quenched with dilute aqueous acid and extractive work-up known in the art affords the mono or diester compounds of Formula Ia, which can be purified by standard methods such as chromatography or recrystallization. Another suitable esterification method is to contact a compound of Formula Ia, in which either $R_1$ and/or $R_2$ are represented by OH, with an alcohol of the formula $HOC_1-C_4$ in the presence of an acid such as sulfuric acid. The esterification is typically conducted at elevated temperatures. The desired compound of Formula Ia can then be recovered from the reaction zone by flash chromatography and optionally purified by recrystallization from a solvent system such as ethyl acetate/hexane.

Another suitable esterification method is to contact a compound of Formula Ia, in which either $R_1$ and/or $R_2$ are represented by OH, with a molar excess of an alcohol of the formula $HOC_1-C_4$, a molar excess of triphenylphoshine, and a molar excess of diethylazodicarboxylate. The reactants are typically contacted in an anhydrous organic solvent, such as tetrahydrofuran. The reactants are typically stirred together for a period of time ranging from 1 hour to 24 hours and at a temperature range of from 0° C. to room temperature. The ester derivative is recovered from the reaction by techniques such as flash chromatography. It can then be optionally purified by recrystallization from a solvent system such as ethyl acetate/hexane.

Amides can also be prepared by contacted esters of Formula Ia, in which either $R_1$ and/or $R_2$ are represented by $-OC_1C_4$ with an amine of the formula $HNR_3R_4$ at a temperature of from 0°–100° C. for a period of time ranging from 1–48 hours in an intert solvent such as tetrahydrofuran. The resulting amide derivative of Formula Ia can then be isolated and purified by techniques known in the art.

The starting materials for use in the general synthetic procedure outlined in Scheme I are readily available to one of ordinary skill in the art.

A general synthetic procedure for the preparation of compounds of Formula Ib is set forth in Scheme II. In Scheme II, all substituents, unless otherwise indicated, are as previously defined.

Scheme II

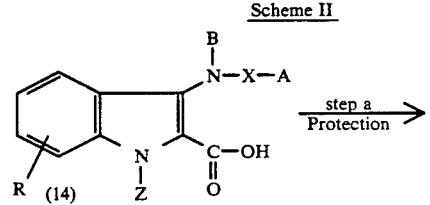

-continued
Scheme II

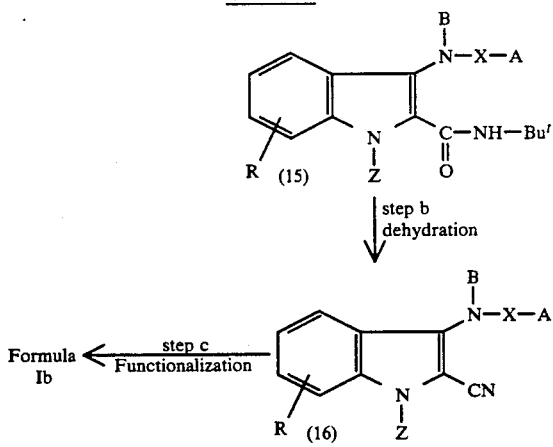

In general, an appropriate 3-amidoindolyl derivative of Formula Ib can be prepared in a multi-step synthesis.

In Scheme II step a, the 2-carboxyindolyl derivative (14) prepared as described previously in Scheme I, is treated with a chlorinating agent such as thionyl chloride in an organic solvent such as toluene with heat, followed by treatment with tert-butylamine to yield the appropriately substituted 2-carboxamidoindole of structure (15).

In Scheme II step b, the 2-carboxamidoindolyl derivative of structure (15) can then be dehydrated by treatment with trifluoroacetic anhydride in an organic solvent such as methylene chloride at room temperture to provide the 2-cyanoindolyl derivative of structure (16).

In Scheme II step c, the 2-cyanoindoyl derivative of structure (16) can then be treated with tributyltin chloride and sodium azide in an organic solvent such as N-methylpyrrolidinone at 70° C. for approximately 70 hours (Carini, D. J. et al. J.Med.Chem. (1991), 34, 1834). After cooling, a workup and purification familiar to one skilled in the art will yield the appropriately substituted 2-tetrazoleindole as described by Formula Ib.

A general synthetic procedure for the preparation of compounds of Formula Ia where A and/or $R_1$ can be a tetrazole substituent is set forth in Scheme III. In Scheme III, all substituents, unless otherwise indicated, are as previously defined.

Scheme III

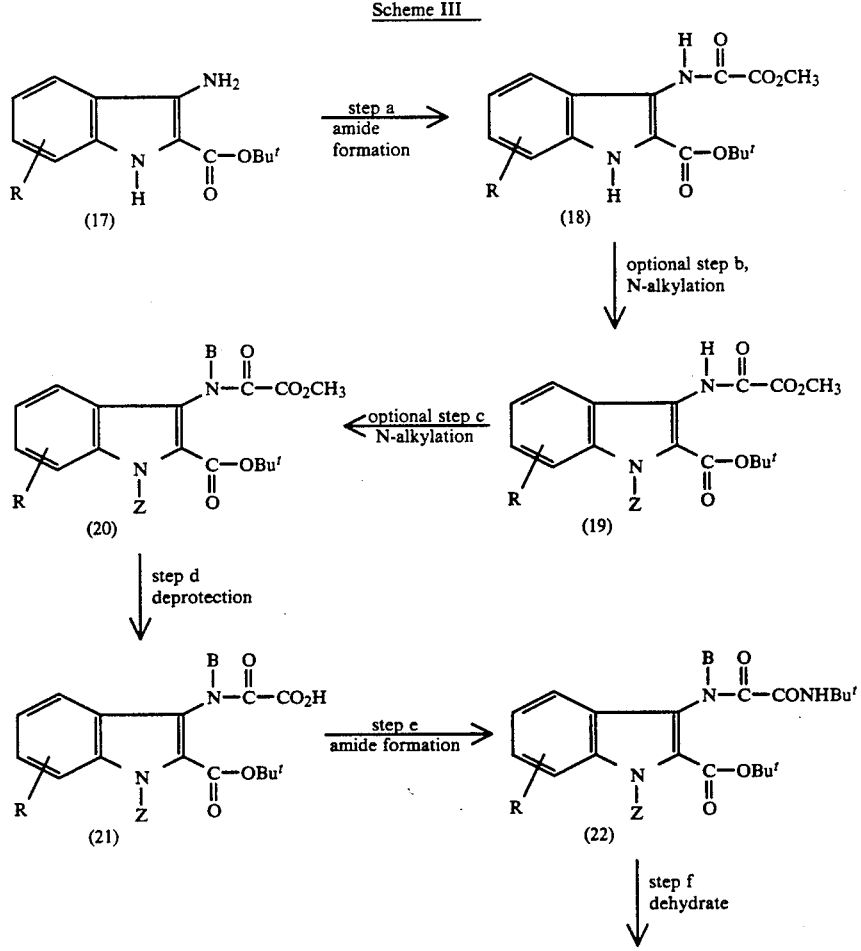

Scheme III

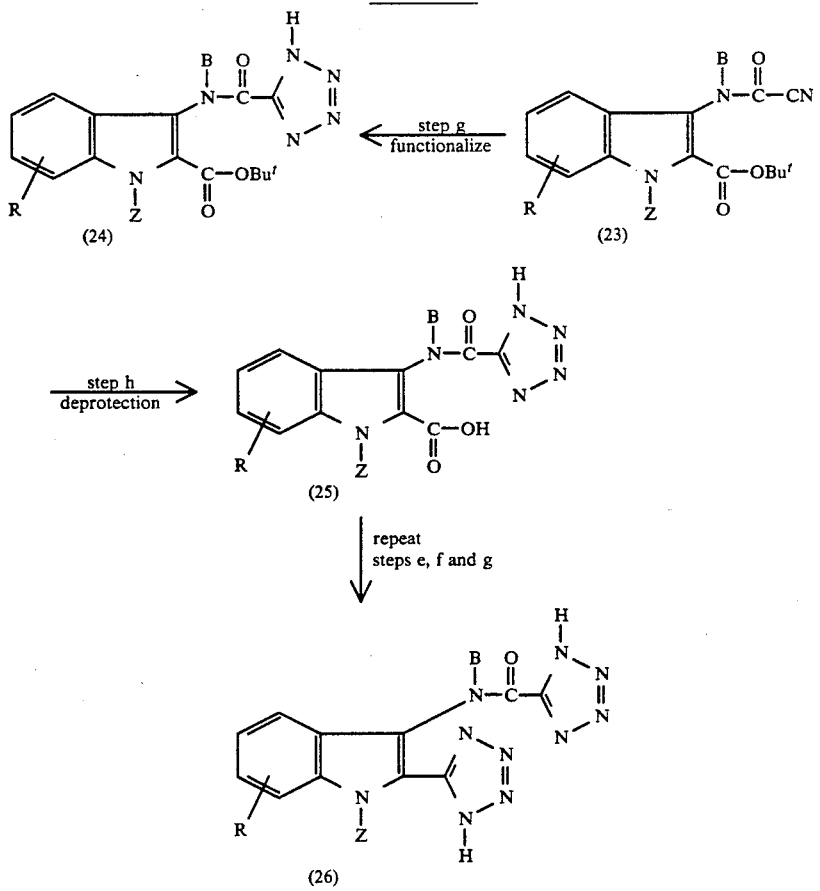

In general, an appropriate 3amidoindolyl derivative of Formula Ia, where A and/or $R_1$ are tetrazole substituents, can be prepared in a multi-step process.

In Scheme III step a, the appropriately substituted 3-aminoindole of structure (17) can be treated with an equivalent of methyl oxalyl chloride, in the presence of an organic amine acid scavenger, in an organic solvent such as tetrahydrofuran at room temperature to provide the 3-amidoindolyl derivative of structure (18).

The 3-aminoindolyl derivative of structure (18) can optionally be N-alkylated in Scheme III step b, following the procedure previously set forth in Scheme I to provide the 3-aminoindolyl derivative of structure (19).

The 3-aminoindolyl derivative of structure (19) can again be optionally N-alkylated in Scheme III step c, following the procedure previously set forth in Scheme I to provide the 3-aminoindolyl derivative of structure (20).

The appropriately substituted 3-aminoindole of structure (20) can then be selectively deprotected by treatment with one equivalent of base such as lithium hydroxide in a solvent mixture such as tetrahydrofuran/water at room temperature to provide the monoacid of structure (21).

The monoacid of structure (21) can then be converted to the amide derivative of structure (22) by treatment with triphenylphosphine, diethyl azodicarboxylate and N-hydroxysuccinimide in an organic solvent such as tetrahydrofuran to provide the succinimide ester. This is then treated with tert-butylamine at room temperature in an organic solvent such as tetrahydrofuran to provide the amide derivative of structure (22).

This can then be converted to the tetrazole derivative of structure (24) by following steps f and g which have been previously described in Scheme II, steps b and c. Compound (24) can then be deprotected by treatment with trifluoroacetic acid in an organic solvent such as methylene chloride at room temperature to provide the tetrazole derivative of structure (25).

Steps e, f and g of Scheme III can then be repeated on the 2-carboxyindolyl derivative of structure (25) to provide the appropriately substituted ditetrazole derivative of structure (26).

A general synthetic procedure for the preparation of compounds of Formula Ic is set forth in Scheme IV. In Scheme IV, all substituents unless otherwise indicated are as previously defined.

Scheme IV

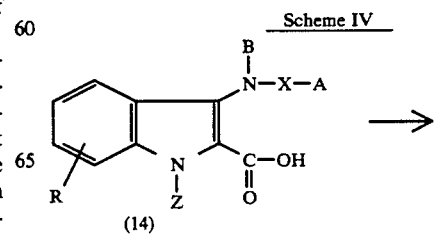

-continued
Scheme IV

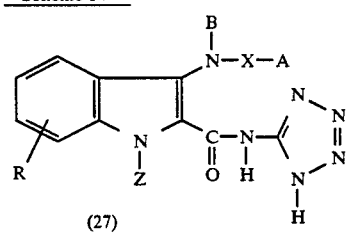

(27)

In general, an appropriate 3-amidoindolyl derivative of Formula Ic can be prepared as described by Scheme IV. The appropriately substituted 3-amidoindolyl of structure (14) can be treated with an excess of a chlorinating reagent such as thionyl chloride in an organic solvent such as toluene at a temperature of 23°-80° C. for 1 hour to 6 hours. The resulting acid chloride of structure (14) is then treated with a molar equivalent of 5-aminotetrazole in an organic solvent such as methylene chloride at room temperature for 1 hour to 1 day to provide the 3-amidoindolyl derivative of structure (27).

The starting materials for use in the general synthetic procedures outlined in Schemes II, III and IV are available to one skilled in the art.

The following examples present typical syntheses as described by Scheme I through Scheme IV. These examples are understood to be illustrative only and are not intended to limit the scope of the invention in any way. As used in the following examples, the following terms have the meanings indicated: "g" refers to grams, "mmol" refers to millimoles, "mL" refers to milliliters, "° C." refers to degrees Celsius, "TLC" refers to thin layer chromatography, "mg" refers to milligrams, "μL" refers to microliters, "eq" refers to equivalents.

EXAMPLE 1

Preparation of 3-[(2-Acetoxyphenacyl)amino]-2-carbmethoxy-6-chloroindole

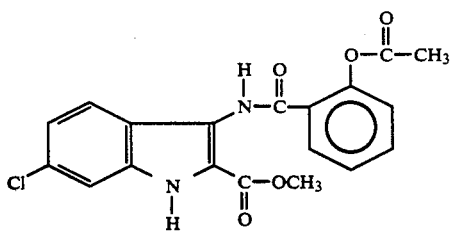

Step a:
2-(Carbmethoxy)methylamino-4-chlorobenzonitrile

Dissolve 2-amino-4-chlorobenzonitrile (12.9 g, 85 mmol) in anhydrous dimethylformamide (15 mL). Add potassium carbonate (7.6 g, 90 mmol) and methyl bromoacetate (7.8 mL, 90 mmol) and stir at 70° C. for 5 days. Add additional methyl bromoacetate (78 mL, 90 mmol) and continue heating for 1 day. Dilute with ethyl acetate (300 mL), wash with water, separate the organic phase and dry (MgSO4). Evaporate the solvent in vacuo and purify by flash chromatography (25% ethyl acetate/hexane). Recrystallize (hexane) to give the title compound (7 g, 36%).

Step b: 3-Amino-2-carbmethoxy-6-chloroindole

Dissolve potassium tert-butoxide (44 mmol) in anhydrous tetrahydrofuran (80 mL) and cool to 5° C. Add a solution of 2-(carmethoxy)methylamino-4-chlorobenzonitrile (10 g, 44 mmol) in anhydrous tetrhydrofuran (80 mL). Allow to warm to room temperature and stir for 3 hours. Pour into water/ethyl acetate, separate the organic phase and dry (MgSO4). Evaporate the solvent in vacuo and purify by flash chromatography (25% ethyl acetate/hexane followed by 50% ethyl acetate/hexane) and recrystallize (ethyl acetate/hexane) to give the title compound; first crop (5.5 g, 55%) and second crop (1.9 g, 19%).

Step c:
3-[(2-Acetoxyphenacyl)amino]-2-carboxy-6-chloroindole

Dissolve 3-amino-2-carbmethoxy-6-chloroindole (1 g, 4.4 mmol) in anhydrous tetrahydrofuran (50 mL). Add triethylamine (4.8 mmol) and acetylsalicoyl chloride (4.8 mmol) and stir for 5 minutes. Dilute into ethyl acetate (500 mL), separate the organic phase, wash with water, saturated sodium hydrogen carbonate and saturated sodium chloride. Dry and evaporate the solvent in vacuo. Recrystallize to give the title compound (1.3 g, 79%); mp 184°-86° C.

Anal. Calcd for $C_{19}H_{15}ClN_2O_5$: C, 59.00; H, 3.91; N, 7.24; Found: C, 58.90; H, 3.88; N, 7.11.

EXAMPLE 2

Preparation of 3-[(2-Hydroxyphenacyl)amino]-2-carboxy-6-chloroindole

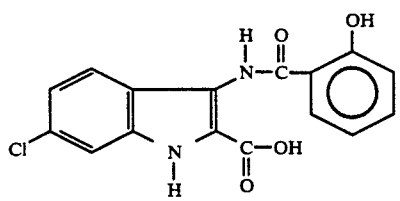

Dissolve 3-[(2-acetoxyphenacyl)amino]-2-carbmethoxy-6-chloroindole (800 mg, 2.15 mmol) in tetrahydrofuran/water (20 mL, 1/1). Add lithium hydroxide monohydrate (932 mg, 8.5 mmol). Seal the flask and warm to 60° C. for 3 hours. Dilute with ethyl acetate/water, acidify and separate the organic phase. Dry, precipitate with hexane and filter the solid to give the title compound (358 mg, 50%); mp 198°-200° C.

EXAMPLE 3

Preparation of 3-[(Phenacyl)amino]-2-carbmethoxy-6-chloroindole

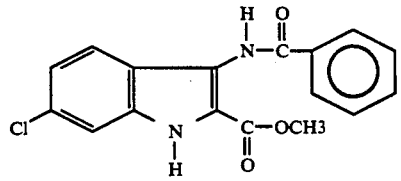

Dissolve 3-amino-2-carbmethoxy-6-chloroindole (500 mg, 2.22 mmol) in methylene chloride (10 mL). Add triethylamine (334 μL, 2.4 mmol) and benzoyl chloride (2.4 mmol) and stir for hour. Dilute into ethyl acetate (300 mL), wash with water and saturated sodium chloride. Dry and evaporate the solvent in vacuo. Recrystallize to give the title compound; first crop (570 mg, 78%) and second crop (70 mg, 9%); mp 242°–43° C.

EXAMPLE 4

Preparation of 3-[(Phenacyl)amino]-2-carboxy-6-chloroindole

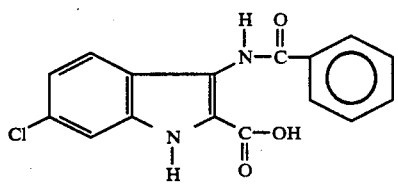

Dissolve 3-[(phenacyl)amino]-2-carbmethoxy-6-chloroindole (480 mg, 1.46 mmol) in tetrahydrofuran/water (20 mL, 1/1). Add lithium hydroxide monohydrate (316 mg, 2.92 mmol). Seal the flask and warm to 60° C. for 3 hours. Dilute with ethyl acetate/water (50 mL/50 mL) and separate the organic phase. Acidify the aqueous phase and extract with ethyl acetate. Dry (MgSO4) the combined organic phases and concentrate in vacuo. Precipitate with hexane to give the title compound; first crop (289 mg, 63%) and second crop (74 mg, 16%); mp 205°–210° C. (dec).

Example 4a

Preparation of 3-[(phenacyl)methylamino]-2-carbmethoxy-6-chloroindole

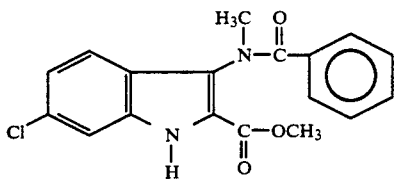

Scheme I, step d2:
3-[(phenacyl)amino]-2-carbmethoxy-6-chloro-1-(tert-butyloxycarbonyl)-indole Mix 3-[(phenacyl)amino]-2-carbmethoxy-6-chloroindole (130 mg, 0.395 mmol), di-tert-butyl dicarbonate (89 mg, 0.395 mmol), tetrahydrofuran (5 mL), dimethylaminopyridine (4 mg) and stir at room temperture overnight. Dilute the reaction with ethyl acetate (25 mL), wash with water, dry over magnesium sulfate, filter and concentrate in vacuo. Recrystallize the residue from ethyl acetate/hexane to yield the title compound as a white fluffy solid (160 mg, 95%).

Scheme I, step e:
3-[(phenacyl)methylamino]-2-carbmethoxy-6-chloro-1-(tert-butyloxycarbonyl)-indole Suspend sodium hydride (14.4 mg of a 60% dispersion, 0.36 mmol) in anhydrous tetrahydrofuran (1 mL) and cool to 0° C. under a nitrogen atmosphere. Add 3-[(phenacyl)amino]-2-carbmethoxy-6-chloro-1-(tert-butyloxycarbonyl)-indole (140 mg, 0.326 mmol) in tetrahydrofuran/dimethylformamide (2 mL, 3:1) dropwise to the suspension. Stir at 0° C. for 30 minutes. Add methyl iodide (0.0224 mL, 0.36 mmol) and stir for 30 minutes at 0° C. Warm the reaction to room temperature and quench with water ad extract with ethyl acetate. Rinse the organic phase with saturated sodium chloride, dry over magnesium sulfate, filter and concentrate in vacuo to yield the title compound (130 mg).

Scheme I, step f:
3-[(phenacyl)methylamino]-2-carbmethoxy-6-chloroindole

Dissolve 3-[(phenacyl)methylamino]-2-carbmethoxy-6-chloro-1-(tert-butyloxycarbonyl)-indole from above in methylene chloride (3 mL). Add trifluoracetic acid (1 mL) and stir for 2 hours. Dilute into ethyl acetate and rinse with saturated sodium bicarbonate. Dry the organic phase over magnesium sulfate, filter and concentrate in vacuo to yield the title compound.

Example 4b

Preparation of 3-[(phenacyl)methylamino]-2-carboxy-6-chloroindole

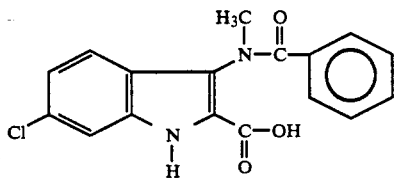

Dissolve 3-[(phenacyl)methylamino]-2-carbmethoxy-6-chloroindole from above, in tetrahydrofuran (5 mL) and water (5 mL). Add lithium hydroxide and stir for 8 hours at 40° C. Dilute the reaction with water (10 mL) and ethyl acetate (10 mL). Separate the layers and acidify the aqueous layer. Extract the aqueous with ethyl acetate, dry the organic phase over magnesium sulfate, filter and concentrate in vacuo. Recrystallize from ethyl acetate/hexane to yield the title compound (75 mg); mp 250°–255° C.

Anal. Calcd for $C_{17}H_{13}ClN_2O_3$: C, 62.11; H, 3.99; N, 8.52; Found: C, 61.77; H, 4.20; N, 8.62.

Example 4c

Preparation of 3-[(m-fluorophenacyl)amino]-2-carbmethoxy-6-chloroindole

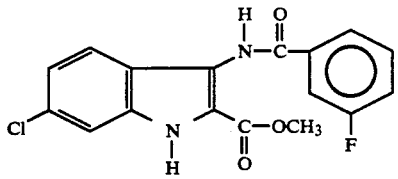

Suspend the 3-amino-2-carbmethoxy-6-chloroindole (1 g, 4.45 mmol) in methylene chloride (50 mL) and add triethylamine (0.416 mL, 4.6 mmol) to produce a mostly clear solution. Add the m-fluorobenzoyl chloride (0.561 mL, 4.6 mmol) and stir for five minutes at room temperature to produce a thick white precipitate. Dilute the reaction with ethyl acetate (700 mL), rinse with water, dry over magnesium sulfate, filter and concentrate in vacuo to 300 mL. Recrystallize by adding hot hexane (150 mL) to the already hot solution of ethyl acetate to yield the title compound.

Example 4d

Preparation of 3-[(m-fluorophenacyl)methylamino]-2-carbmethoxy-6-chloroindole

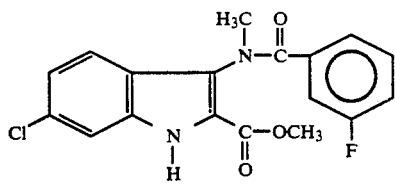

Scheme I, step d₂:
3-[(m-fluorophenacyl)amino]-2-carbmethoxy-6-chloro-1-(tert-butyloxycarbonyl)-indole Mix 3-[(m-fluorophenacyl)amino]-2-carbmethoxy-6-chloroindole (1.5 g, 4.3 mmol), di-tert-butyl dicarbonate (982 mg, 4.5 mmol), tetrahydrofuran (5 mL), dimethylaminopyridine (42 mg, 0.4 mmol) and stir for several minutes. Dilute the reaction with ethyl acetate, wash with water, dry over magnesium sulfate, filter and concentrate in vacuo to yield the title compound.

Scheme I, step e:
3-[(m-fluorophenacyl)methylamino]-2-carbmethoxy-6-chloro-1-(tert-butyloxycarbonyl)-indole Suspend sodium hydride (120 mg of a 60% dispersion, 3 mmol) in anhydrous tetrahydrofuran (3 mL) and cool to 0° C. under a nitrogen atmosphere. Add 3-[(phenacyl)amino]-2-carbmethoxy-6-chloro-1-(tert-butyloxycarbonyl)-indole (1.3 g, 2.9 mmol) in tetrahydrofuran/dimethylformamide (10 mL, 3:1) dropwise to the suspension producing a clear yellow solution at 15 minutes. Stir at 0° C. for 30 minutes. Add methyl iodide (0.186 mL, 3 mmol). Warm the reaction to room temperature and stir overnight. Quench with water (20 mL) and extract with ethyl acetate (20 mL). Rinse the organic phase with saturated sodium chloride, dry and concentrate in vacuo to yield the title compound.

Scheme I, step f:
3-[(m-fluorophenacyl)methylamino]-2-carbmethoxy-6-chloroindole Dissolve 3-[(m-fluorophenacyl)methylamino]-2-carbmethoxy-6-chloro-1-(tert-butyloxycarbonyl)-indole from above in methylene chloride (5 mL). Add trifluoroacetic acid (5 mL) and stir for 4 hours at room temperture. Dilute with ethyl acetate (50 mL) and rinse with 1N sodium hydroxide, saturated sodium chloride, dry over magnesium sulfate, filter and concentrate in vacuo. Purify the residue by flash chromatography (30% ethyl acetate/hexane) and recrystallize from ethyl acetate/hexane to yield the title compound (700 mg, 70%).

Example 4e

Preparation of 3-[(m-fluorophenacyl)methylamino]-2-carboxy-6-chloroindole

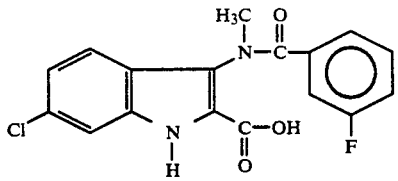

Dissolve 3-[(m-fluorophenacyl)methylamino]-2-carbmethoxy-6-chloroindole (650 mg, 1.8 mmol) in tetrahydrofuran (10 mL) and water (10 mL). Add lithium hydroxide (227 mg, 5.4 mmol). Add methanol dropwise until an homogeneous solution forms. Stir the reaction at room temperature overnight. Dilute the reaction with water(10 mL) and ethyl acetate (25 mL). Acidify with 1N HCl and separate the layers. Dry the organic phase over magnesium sulfate, filter and concentrate 50% with heat. Reconstitute with hot hexane. Repeat the concentration and reconstitution steps and cool to yield the title compound (550 mg, 89%); mp 258°–260° C.

Anal. Calcd for $C_{17}H_{12}ClFN_2O_3$: C, 58.88; H, 3.49; N, 8.08; Found: C, 58.63; H, 3.44; N, 7.78.

Example 4f

Preparation of 3-[(p-fluorophenacyl)amino]-2-carbmethoxy-6-chloroindole

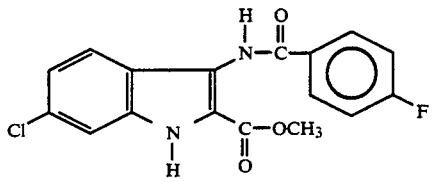

Suspend the 3-amino-2-carbmethoxy-6-chloroindole (1.15 g, 5.12 mmol) in methylene chloride (80 mL) and add triethylamine (0.497 mL, 5.5 mmol). Add the p-fluorobenzoyl chloride (0.650 mL, 5.5 mmol) and stir for 30 minutes at room temperature to produce a precipitate. Dilute the reaction with ethyl acetate (150 mL), rinse with water, dry over magnesium sulfate, filter and concentrate in vacuo to yield the title compound.

Example 4g

Preparation of 3-[(p-fluorophenacyl)methylamino]-2-carbmethoxy-6-chloroindole

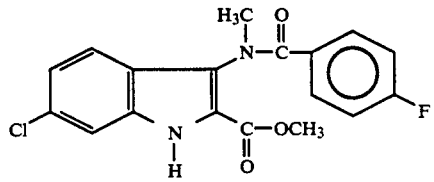

Scheme I, step d₂:
3-[(p-fluorophenacyl)amino]-2-carbmethoxy-6-chloro-1-(tert-butyloxycarbonyl)-indole Mix 3-[(p-fluorophenacyl)amino]-2-carbmethoxy-6-chloroindole (1.7 g, 5.12 mmol), di-tert-butyl dicarbonate (1.13 g, 5.12 mmol), tetrahydrofuran (50 mL), dimethylaminopyridine (52 mg, 0.5 mmol) and stir for 6 hours. Dilute the reaction with ethyl acetate, wash with water, dry over magnesium sulfate, filter and concentrate in vacuo to yield the title compound.

Scheme I, step e:
3-[(p-fluorophenacyl)methylamino]-2-carbmethoxy-6-chloro-1-(tert-butyloxycarbonyl)-indole Suspend sodium hydride (240 mg of a 60% dispersion, 6 mmol) in anhydrous tetrahydrofuran (3 mL) and cool to 0° C. under a nitrogen atmosphere. Add 3-[(p-fluorophenacyl)amino]-2-carbmethoxy-6-chloro-1-(tert-butyloxycarbonyl)-indole (2.5 g, 5.6 mmol) in tetrahydrofuran/dimethylformamide (10 mL, 3:1) dropwise to the suspension producing a clear yellow solution at 15 minutes. Stir at 00C. for 30 minutes. Add methyl iodide (0.371 mL, 6 mmol). Warm the reaction to room temperature and stir overnight. Quench with water (20 mL) and extract with ethyl acetate (20 mL). Rinse the organic phase with saturated sodium chloride, dry and concentrate in vacuo to yield the title compound.

Scheme I, step f:
3-[(p-fluorophenacyl)methylamino]-2-carbmethoxy-6-chloroindole Dissolve 3-[(p-fluorophenacyl)methylamino]-2-carbmethoxy-6-chloro-1-(tert-butyloxycarbonyl)-indole from above in methylene chloride (5 mL). Add trifluoracetic acid (5 mL) and stir for 4 hours at room temperature. Dilute with ethyl acetate (50 mL) and rinse with 1N sodium hydroxide, saturated sodium chloride, dry over magnesium sulfate, filter and concentrate in vacuo. Purify the residue by flash chromatography (30% ethyl acetate/hexane) and recrystallize from ethyl acetate/hexane to yield the title compound (1.0 g, 62%).

Example 4h

Preparation of 3-[(p-fluorophenacyl)methylamino]-2-carboxy-6-chloroindole

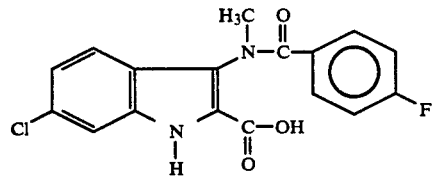

Dissolve 3-[(p-fluorophenacyl)methylamino]-2-carbmethoxy-6-chloroindole 650 mg, 1.8 mmol) in tetrahydrofuran (10 mL) and water (10 mL). Add lithium hydroxide (227 mg, 5.4 mmol). Add methanol dropwise until an homogeneous solution forms. Stir the reaction at room temperature overnight. Dilute the reaction with water(10 mL) and ethyl acetate (25 mL). Acidify with 1N HCl and separate the layers. Dry the organic phase over magnesium sulfate, filter and concentrate 50% with heat. Reconstitute with hot hexane. Repeat the concentration and reconstitution steps and cool to yield the title compound (560 mg, 90%); mp 2480°-2500C.

Anal. Calcd for $C_{17}H_{12}ClFN_2O_3$: C, 58.88; H, 3.49; N, 8.08; Found: C, 58.75; H, 3.43; N, 7.70.

Example 4i

Preparation of 3-[(3,4-difluorophenacyl)amino]-2-6-chloroindole

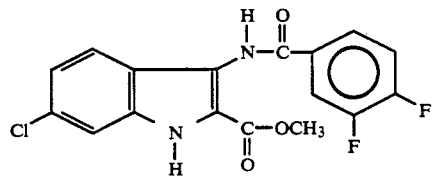

Suspend the 3-amino 2-carbmethoxy-6-chloroindole (1.15 g, 5.2 mmol) in methylene chloride (80 mL) and add triethylamine (0.497 mL, 5.5 mmol). Add the 3,4-difluorobenzoyl chloride (0.692 mL, 5.5 mmol) and stir for 30 minutes at room temperature to produce a precipitate. Dilute the reaction with ethyl acetate, rinse with water, dry over magnesium sulfate, filter and concentrate in vacuo to yield the title

Example 4j

Preparation of 3-[(3,4-difluorophenacyl)methylamino]-2-6-chloroindole

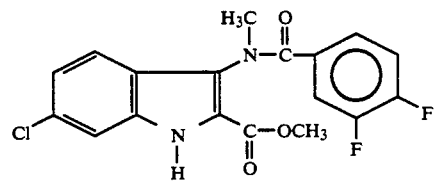

Scheme I, step d₂:
3-[(3,4-difluorophenacyl)amino]-2-carbmethoxy-6-chloro-1-(tert-butyloxycarbonyl)-indole Mix 3-[(3,4-difluorophenacyl)amino]-2-carbmethoxy-6-chloroindole (5.2 mmol), di-tert-butyl dicarbonate (1.19 g, 5.4 mmol), tetrahydrofuran (50 mL), dimethylaminopyridine (52 mg, 0.5 mmol) and stir for 6 hours. Dilute the reaction with ethyl acetate, wash with water, dry over magnesium sulfate, filter and concentrate in vacuo to yield the title compound.

Scheme I, step e:
3-[(3,4-difluorophenacyl)methylamino]-2-carbmethoxy-6-chloro-1-(tert-butyloxycarbonyl)-indole Suspend sodium hydride (188 mg of a 60% dispersion, 4.7 mmol) in anhydrous tetrahydrofuran (3 mL) and cool to 0° C. under a nitrogen atmosphere. Add 3-[(phenacyl)amino]-2-carbmethoxy-6-chloro-1-(tert-butyloxycarbonyl)-indole (2 g, 4.3 mmol) in tetrahydrofuran/dimethylformamide (10 mL, 3:1) dropwise to the suspension producing a clear yellow solution at 15 minutes. Stir at 0° C. for 30 minutes. Add methyl iodide (0.291 mL, 4.7 mmol). Warm the reaction to room temperature and stir overnight. Quench with water (20 mL) and extract with ethyl acetate (20 mL). Rinse the organic phase with saturated sodium chloride, dry and concentrate in vacuo to yield the title compound.

Scheme I, step f:
3-[(3,4-difluorophenacyl)methylamino]-2-carbmethoxy-6-chloroindole Dissolve 3-[(3,4-difluorophenacyl)methylamino]-2-carbmethoxy-6-chloro-1-(tert-butyloxycarbonyl)-indole from above in methylene chloride (5 mL). Add trifluoracetic acid (5 mL) and stir for 4 hours at room temperture. Dilute with ethyl acetate (50 mL) and rinse with 1N sodium hydroxide, saturated sodium chloride, dry over magnesium sulfate, filter and concentrate in vacuo. Purify the residue by flash chromatography (30% ethyl acetate/hexane) and recrystallize from ethyl acetate/hexane to yield the title compound (1.0 g, 62%).

Example 4k

Preparation of
3-[(3,4-difluorophenacyl)methylamino]-2-carboxy-6-chloroindole

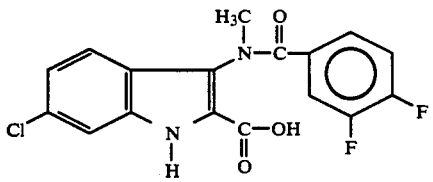

Dissolve 3-[(3,4-difluorophenacyl)methylamino]-2-carbmethoxy-6-chloroindole 650 mg, 1.7 mmol) in tetrahydrofuran (10 mL) and water (10 mL). Add lithium hydroxide (227 mg, 5.4 mmol). Add methanol dropwise until an homogeneous solution forms. Stir the reaction at room temperature overnight. Dilute the reaction with water(10 mL) and ethyl acetate (25 mL). Acidify with 1N HCl and separate the layers. Dry the organic phase over magnesium sulfate, filter and concentrate 50% with heat. Reconstitute with hot hexane. Repeat the concentration and reconstitution steps and cool to yield the title compound (510 mg, 82%); mp 260°-264° C.

Anal. Calcd for $C_{17}H_{11}ClF_2N_2O_3$: C, 55.98; H, 3.04; N, 7.68; Found: C, 56.07; H, 3.06; N, 7.40.

Example 4L

Preparation of
3-[(phenacyl)methylamino]-2-carboxy-6-fluoroindole

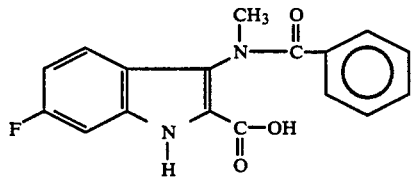

Step 1. Preparation of starting material:
2-amino-4-fluorobenzonitrile;

Suspend 4-fluoro-2-nitro-benzoic acid (4.5 g, 24.3 mmol) in toluene (20 mL), add thionyl chloride (22.5 mL) seal the flask and warm to 50° C. for 3 hours. Concentrate the reaction in vacuo and reconcentrate two more times from toluene. Place under high vacuum for 1 hour. Dissolve the acid chloride in methylene chloride (40 mL) and add t-butylamine (13.5 mL). Stir the reaction at room temperture. Concentrate the reaction in vacuo to yield the 4-fluoro-2-nitro-tert-butylbenzamide as an off white solid (5.5 g, 95%); mp 142°-143° C.

Anal. Calcd for $C_{11}H_{13}FN_2O_3$: C, 55.00; H, 5.45; N, 11.66; Found: C, 55.09; H, 5.19; N, 11.63.

Step 2. Dissolve the above product (5 g, 21 mmol) in ethanol (20 mL) and purge the flask with nitrogen. Add 10% palladium on carbon (200 mg) and place under hydrogen at 50 psi. Shake the reaction for 2 hours. Filter the reaction through diatomaceous earth and concentrate the filtrate in vacuo. Purify the residue by flash chromatography (25% ethyl acetate/hexane) and recrystallize the purified product from ethyl acetate/hexane to yield the 4-fluoro-2-amino-tert-butylbenzamide; mp 1160°-1170C.

Anal. Calcd for $C_{11}H_{15}FN_2O$: C, 62.84; H, 7.19; N,13.32; Found: C, 62.74; H, 6.94; N, 13.08.

Step 3. Dissolve the above product (2.87 g, 14.24 mmol) in methylene chloride (70 mL) and add trifluoroacetic anhydride (10 mL, 71 mmol). Stir the reaction at room temperature for 8 hours under a nitrogen atmosphere. Rinse the reaction with saturated sodium bicarbonate and concentrate in vacuo. Recrystallize the residue from methylene chloride/hexane to yield the 2-trifluoromethylacetamide-4-fluorobenzonitrile as colorless needles (3.2 g, 97%); 104°-105° C.

Anal. Calcd for $C_9H_4F_4N_2O$: C, 46.56; H, 1.74; N, 12.07; Found: C, 46.67; H, 1.53; N, 12.09.

Scheme I, step a:
2-(Carbethoxy)methylamino-4-fluorobenzonitrile

Dissolve the 2-trifluoromethylacetamide-4-fluorobenzonitrile (1 g, 4.3 mmol) in dimethylformamide (4 mL) under an atmosphere of nitrogen. Add ethyl bromoacetate (0.954 mL, 8.6 mmol), potassium carbonate (1.1 g, 8.6 mmol) and heat to 50° C. for 2.5 hours. Dilute the reaction with ethyl acetate and rinse the organic phase with water. Dry the organic phase, filter and concentrate in vacuo to yield the title compound (1.1 g).

Scheme I, step b: 3-Amino-2-carbethoxy-6-fluoroindole

Dissolve 2-(Carbethoxy)methylamino-4-fluorobenzonitrile (220 mg, 1 mmol) in tetrahydrofuran (3 mL) and add dropwise with stirring to a solution of potassium tert-butoxide (1 mL of a 1M solution in 1 mL tetrahydrofuran) under a nitrogen atmosphere. After 1 hour, dilute with ethyl acetate, rinse with water, dry the organic phase and concentrate in vacuo to yield the title compound (170 mg, 77%).

Scheme I, step c:
3-[(Phenacyl)amino]-2-carbethoxy-6-fluoroindole

Suspend 3-Amino-2-carbethoxy-6-fluoroindole (1.1 eq) in methylene chloride and add triethylamine (1.1 eq). Add benzoyl chloride (1.1 eq) and stir for 30 minutes at room temperature to produce a precipitate. Dilute the reaction with ethyl acetate, rinse with water, dry over magnesium sulfate, filter and concentrate in vacuo to yield the title compound (1.26 g).

Scheme I, step d₂:
3-[(phenacyl)amino]-2-carbethoxy-6-fluoro-1-(tert-butyloxycarbonyl)-indole Mix 3-[(phenacyl)amino]-2-carbethoxy-6-fluoroindole (1.0 g, 3.06 mmol), di-tert-butyl dicarbonate (0.70 g, 3.2 mmol), tetrahydrofuran (40 mL), dimethylaminopyridine (33 mg, 0.32 mmol) and stir overnight. Dilute the reaction with ethyl acetate, wash with water, saturated sodium chloride, dry over magnesium sulfate, filter and concentrate in vacuo. Recrystallize from ethyl acetate/hexane followed by flash chromatography (20% ethyl acetate/hexane). Recrystallize again from ethyl acetate/hexane to yield 3-[(phenacyl)amino]-2-carbethoxy-6-fluoro-1-(tert-butyloxycarbonyl)-indole as colorless needles (900 mg, 69%).

Scheme I, step e:
3-[(phenacyl)methylamino]-2-carbethoxy-6-fluoro-1-(tert-butyloxycarbonyl)-indole Suspend sodium hydride (62 mg of a 60% dispersion, 1.55 mmol) in anhydrous tetrahydrofuran (3 mL) and cool to 0° C. under a nitrogen atmosphere. Add 3-[(phenacyl)amino]-2-carbethoxy-6-fluoro-1-(tert-butyloxycarbonyl)-indole (650 mg, 1.52 mmol) in tetrahydrofuran/dimethylformamide (10 mL, 3:1) dropwise to the suspension producing a clear yellow solution at 15 minutes. Stir at 0° C. for 30 minutes. Add methyl iodide (0.096 mL, 1.55 mmol). Warm the reaction to room temperature and stir overnight. Quench with water (20 mL) and extract with ethyl acetate (20 mL). Rinse the organic phase with saturated sodium chloride, dry and concentrate in vacuo to yield the 3-[(phenacyl)methylamino]-2-carbethoxy-6-fluoro-1-(tert-butyloxycarbonyl)-indole.

Scheme I, step f:
3-[(phenacyl)methylamino]-2-carbethoxy-6-fluoroindole

Dissolve 3-[(phenacyl)methylamino]-2-carbethoxy-6-fluoro-1-(tert-butyloxycarbonyl)-indole from above in methylene chloride (10 mL). Add trifluoracetic acid (3 mL) and stir for 4 hours at room temperature. Dilute with ethyl acetate (50 mL) and rinse with 1N sodium hydroxide, saturated sodium chloride, dry over magnesium sulfate, filter and concentrate in vacuo to yield 3-[(phenacyl)methylamino]-2-carbethoxy-6-fluoroindole.

Dissolve 3-[(phenacyl)methylamino]-2-carbethoxy-6-fluoroindole (300 mg) in tetrahydrofuran and water. Add lithium hydroxide. Stir the reaction at room temperature overnight. Dilute the reaction with water and ethyl acetate. Acidify with 1N HCl and separate the layers. Dry the organic phase over magnesium sulfate, filter and concentrate in vacuo. Recrystallize from ethyl acetate/hexane to yield the title compound as a white powder (270 mg); mp 265°-270° C.

Anal. Calcd for $C_{17}H_{13}FN_2O_3$: C, 65.38; H, 4.20; N, 8.97; Found: C, 65.25; H, 4.20; N, 8.82.

Example 4m

Preparation of
3-[(phenacyl]methylamino]-2-carboxy-6-trifluoromethylindole

Step 1. Preparation of starting material:
2-amino-4-trifluoromethylbenzonitrile

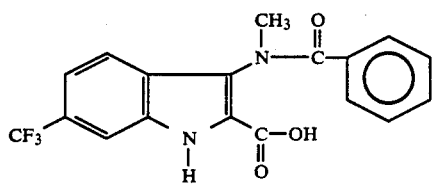

suspend 4-trifluoromethyl-2-nitro-benzoic acid (1 g, 4.25 mmol) in toluene (5 mL), add thionyl chloride (5 mL) and reflux for 1.5 hours. Concentrate the reaction in vacuo and reconcentrate two more times from toluene. Place under high vacuum for 1 hour. Dissolve the acid chloride in toluene (5 mL) and add excess t-butylamine. Stir the reaction at room temperture. Dilute the reaction with ethyl acetate and wash with 1M HCl (3×100 mL), dry over magnesium sulfate, filter and concentrate in vacuo to give a white solid. Recrystallize from hot ethyl acetate/hexane to yield 2-nitro-4-trifluoromethyl-tert-butylbenzamide as white crystals (0.96 g, 81%); mp 162°-640° C.

Step 2. Dissolve 2-nitro-4-trifluoromethyl-tert-butylbenzamide (520 mg, 1.79 mmol) in ethanol (100 mL) and purge the flask with nitrogen. Add 5% palladium on carbon (50 mg) and place under hydrogen at 50 psi. Shake the reaction for 2 hours. Filter the reaction through diatomaceous earth and concentrate the filtrate in vacuo to yield a white solid. Purify the residue by flash chromatography (20% ethyl acetate/hexane) to yield the 2-amino-4-trifluoromethyl-tert-butylbenzamide as white crystals (280 mg, 69% based on recovered starting material); mp 109°-110° C.

Step 3. Dissolve 2-amino-4-trifluoromethyl-tert-butylbenzamide (850 mg, 3.26 mmol) in methylene chloride and add trifluoroacetic anhydride (4.62 mL, 32.7 mmol). Stir the reaction at room temperature for 6 hours under a nitrogen atmosphere. Rinse the reaction with saturated sodium bicarbonate, water and concentrate in vacuo to provide an off white solid. Recrystallize from ethyl acetate/hexane to yield the 2-trifluoromethylacetamide-4-trifluoromethylbenzonitrile (640 mg, 69.5%); 118°-119° C.

Scheme I, step a:
2-(Carbethoxy)methylamino-4-trifluoromethylbenzonitrile

Dissolve 2-trifluoromethylacetamide-4-trifluoromethylbenzonitrile (5.44 g, 19.28 mmol) in dimethylformamide (30 mL) under an atmosphere of nitrogen. Add this to a suspension of sodium hydride (848 mg 60% dispersion, 21.21 mmol) in dimethylformamide (2 mL) at 0° C. Warm the solution to room temperature over 40 minutes. Add ethyl bromoacetate (4.276 mL, 38.6 mmol) to the solution and heat to 50° C. for 40 minutes. Pour the reaction into water and extract with diethyl ether. Separate the layers and rinse the organic phase with saturated sodium chloride, dry over magnesium sulfate, filter and concentrate in vacuo. Purify the residue by flash chromatography (50% methanol:-chloroform/hexane, 3/2) and recrystallize from hot ethyl acetate/hexane to yield the trifluoroacetate derivative (5.83 g, 81.7%); mp 79°-80° C.

Dissolve the above carbethoxy derivative (4.9 g, 13.31 mmol) in ethanol/water and treat with potassium carbonate (1.837 g, 13.31 mmol). Dilute with water and extract with ethyl acetate. Rinse the organic layer with saturated sodium chloride, water, dry over magnesium sulfate, filter and concentrate in vacuo to yield a yellow solid. Recrystallize from hot ethyl acetate/hexane to yield 2-(Carbethoxy)methylamino-4-trifluoromethylbenzonitrile (2.78 g, 76.8%); mp 980°-101° C.

Scheme I, step b:
3-Amino-2-carbethoxy-6-trifluoromethylindole

Dissolve 2-(Carbethoxy)methylamino-4-trifluoromethylbenzonitrile (2.34 g, 8.6 mmol) in tetrahydrofuran (40 mL) and add dropwise with stirring to a solution of potassium tert-butoxide (9.46 mL of a 1M tetrahydrofuran solution) under a nitrogen atmosphere at 0° C. The reaction was allowed to warm to room temperature. After 3 hour, dilute with ethyl acetate, rinse with water, saturated sodium chloride, dry magnesium sulfate, filter and concentrate in vacuo. Purify the residue by flash chromatography to yield the 3-amino-2-carbethoxy-6-trifluoromethylindole (1.22 g, 52%); mp 204°–210° C.

Scheme I, step c:
3-[(Phenacyl)amino]-2-carbethoxy-6-trifluoromethylindole

Suspend the 3-amino-2-carbethoxy-6-trifluoromethylindole (290 mg, 1.06 mmol) in tetrahydrofuran (30 mL) and add triethylamine (0.150 mL, 1.17 mmol). Add benzoyl chloride (0.136 mL, 1.17 mmol) and stir for 30 minutes at room temperature. Dilute the reaction with ethyl acetate rinse with 1M HCl, water, dry over magnesium sulfate, filter and concentrate in vacuo. Recrystallize from hot ethyl acetate/hexane to yield 3-[(phenacyl)amino]-2-carbethoxy-6-trifluoromethylindole (230 mg, 56%); mp 237°–239° C.

Scheme I, step d$_2$:
3-[(phenacyl)amino-]-2-carbethoxy-6-trifluoromethyl-1-(tert-butyloxycarbonyl)-indole Mix 3-[(phenacyl)amino]-2-carbethoxy-6-trifluoromethylindole (390 mg, 1.04 mmol), di-tert-butyl dicarbonate (249 mg, 1.14 mmol), tetrahydrofuran (10 mL), dimethylaminopyridine (33 mg, 0.32 mmol) and stir overnight. Dilute the reaction with ethyl acetate, wash with 1M HCl, water, dry over magnesium sulfate, filter and concentrate in vacuo. Purify by flash chromatography (15% ethyl acetate/hexane) to yield the title compound as an amber oil (320 mg, 66%).

Scheme I, step e:
3-[(phenacyl)methylamino]-2-carbethoxy-6-trifluoromethyl-1-(tert-butyloxycarbonyl)-indole Suspend sodium hydride (30 mg of a 60% dispersion, 0.739 mmol) in anhydrous tetrahydrofuran (10 mL) and cool to 0° C. under a nitrogen atmosphere. Add 3-[(phenacyl)amino]-2-carbethoxy-6-trifluoromethyl-1-(tert-butyloxycarbonyl)-indole (320 mg, 0.672 mmol) in tetrahydrofuran (20 mL) dropwise to the suspension. Stir at room temperature for 20 minutes. Add methyl iodide (0.0.050 mL, 0.81 mmol). After 3 hours quench with 1M HCl, extract with ethyl acetate and rinse the organic phase with saturated sodium chloride, dry and concentrate in vacuo. Purify the residue by flash chromatography (20% ethyl acetate/hexane) to yield the 3-[(phenacyl)methylamino]-2-carbethoxy-6-trifluoromethyl-1-(tert-butyloxycarbonyl)-indole as a colorless oil (200 mg, 60.6%).

Scheme I, step f:
3-[(phenacyl)methylamino]-2-carbethoxy-6-trifluoromethylindole Dissolve 3-[(phenacyl)methylamino]-2-carbethoxy-6-trifluoromethyl-1-(tert-butyloxycarbonyl)indole (200 mg, 0.407 mmol) from above in methylene chloride. Add trifluoracetic acid and stir overnight at room temperture. Concentrate the reaction in vacuo, dilute with ethyl acetate and rinse with saturated sodium bicarbonate, dry over magnesium sulfate, filter and concentrate in vacuo to yield 3-[(phenacyl)methylamino]-2-carbethoxy-6-trifluoromethylindole as a foam (154 mg, 97%).

Dissolve 3-[(phenacyl)methylamino]-2-carbethoxy-6-trifluoromethylindole (154 mg, 0.395 mmol) in tetrahydrofuran and water. Add lithium hydroxide (50 mg, 1.18 mmol). Stir the reaction at room temperature for 6 hours. Acidify with 1N HCl extract with ethyl acetate and separate the layers. Dry the organic phase over magnesium sulfate, filter and concentrate in vacuo. Recrystallize from ethyl acetate/hexane to yield the title compound as an off white solid (95 mg, 66%); mp 258°–261° C.

Anal. Calcd for $C_{18}H_{13}F_3N_2O_3H_2O$: C, 56.84; H, 3.98; N, 7.37; Found: C, 56.55; H, 3.74; N, 7.04.

Example 4n

Preparation of 3-[(phenacyl)methylamino]-2-carboxy-6-nitroindole

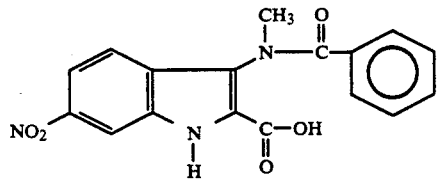

Step 1. Preparation of starting material: 2-amino-4-nitrobenzonitrile

Dissolve 4-nitro-2-aminobenzoic acid (500 mg, 2.75 mmol) in tetrahydrofuran (10 mL). Add triphenylphosphine (730 mg, 2.75 mL) and N-hydroxysuccinimide (316 mg, 2.75 mmol). Add a solution of diethylazodicarboxylate (0.433 mL, 2.75 mmol) and stir at room temperature under nitrogen for 10 minutes. Add tert-butylamine (1.1 mL, 5.5 mmol) in tetrahydrofuran (5 mL) directly to the reaction to yield after workup the 4-nitro-2-amino-tert-butylbenzamide.

Step 2: Dissolve the above product (300 mg, 1.31 mmol) in methylene chloride and add trifluoroacetic anhydride (3 mL, 6.5 mmol). Stir the reaction at room temperature overnight. Rinse the reaction with saturated sodium bicarbonate, water and concentrate in vacuo. Purify by flash chromatography (25% ethyl acetate/hexane) to yield the 2-trifluoromethylacetamide-4-nitrobenzotrile (250 mg, 73%).

Scheme I, step a:
2-(Carbethoxy)methylamino-4-nitrobenzonitrile

Dissolve 2-trifluoromethylacetamide-4-nitrobenzotrile (250 mg, 0.96 mmol) in dimethylformamide (0.5 mL). Add ethyl bromoacetate (0.222 mL, 2 mmol), potassium carbonate (260 mg, 2 mmol) and warm to 80° C. for 2 hours. Cool the reaction, dilute with ethyl acetate, rinse with water, dry, filter and concentrate in vacuo. Purify the residue by flash chromatography (25% ethyl acetate/hexane) to yield the trifluoroacetate derivative (170 mg).

Dissolve the above product(0.8 mmol) in ethanol/water and treat with potassium carbonate (0.8 mmol). Dilute with water and extract with ethyl acetate. Rinse the organic layer with saturated sodium chloride, water, dry over magnesium sulfate, filter and concentrate in vacuo to yield a yellow solid. Recrystallize from hot ethyl acetate/hexane to yield 2-(Carbethoxy)methylamino-4-nitrobenzonitrile.

Scheme I, step b: 3-Amino-2-carbethoxy-6-nitroindole

Dissolve the above carbethoxy derivative (0.7 mmol) in tetrahydrofuran and add dropwise with stirring to a solution of potassium tert-butoxide (0.7 mL of a 1M tetrahydrofuran solution) under a nitrogen atmosphere at 0° C. The reaction was allowed to warm to room temperature. After 3 hour, dilute with ethyl acetate, rinse with water, saturated sodium chloride, dry magnesium sulfate, filter and concentrate in vacuo. Purify the residue by flash chromatography to yield the 3-amino-2-carbethoxy-6-nitroindole.

Scheme I, step c: 3-[(phenacyl)amino]-2-carbethoxy-6-nitroindole

Suspend the 3-amino-2-carbethoxy-6-nitroindole (0.6 mmol) in tetrahydrofuran (mL) and add triethylamine (0.62 mmol). Add benzoyl chloride (0.62 mmol) and stir for 30 minutes at room temperature. Dilute the reaction with ethyl acetate, rinse with 1M HCl, water, dry over magnesium sulfate, filter and concentrate in vacuo. Recrystallize from hot ethyl acetate/hexane to yield 3-[(phenacyl)amino]-2-carbethoxy-6-nitroindole.

Scheme I, step d$_2$: 3-[(phenacyl)amino]-2-carbethoxy-6-nitro-1-(tert-butyloxycarbonyl)-indole Mix 3-[(phenacyl)amino]-2-carbethoxy-6-nitroindole (0.5 mmol), di-tert-butyl dicarbonate (0.52 mmol), tetrahydrofuran, dimethylaminopyridine (mg, mmol) and stir overnight. Dilute the reaction with ethyl acetate, wash with 1M HCl, water, dry over magnesium sulfate, filter and concentrate in vacuo to yield the 3-[(phenacyl)amino]-2-carbethoxy-6-nitro-1-(tert-butyloxycarbonyl)-indole.

Scheme I, step e: 3-[(phenacyl)methylamino]-2-carbethoxy-6-nitro-1-(tert-butyloxycarbonyl)-indole Suspend sodium hydride (0.4 mmol) in anhydrous tetrahydrofuran and cool to 0° C. under a nitrogen atmosphere. Add 3-[(phenacyl)amino]-2-carbethoxy-6-nitro-1-(tert-butyloxycarbonyl)-indole (0.4 mmol) in tetrahydrofuran (mL) dropwise to the suspension. Stir at room temperature for 20 minutes. Add methyl iodide (0.4 mmol). After 3 hours quench with 1M HCl, extract with ethyl acetate and rinse the organic phase with saturated sodium chloride, dry and concentrate in vacuo to yield the 3-[(phenacyl)methylamino]-2-carbethoxy-6-nitro-1-(tert-butyloxycarbonyl)-indole.

Scheme I, step f: 3-[(phenacyl)methylamino]-2-carbethoxy-6-nitroindole

Dissolve 3-[(phenacyl)methylamino]-2-carbethoxy-6-nitro-1-(tert-butyloxycarbonyl)-indole from above in methylene chloride. Add excess trifluoroacetic acid and stir overnight at room temperture. Concentrate the reaction in vacuo, dilute with ethyl acetate and rinse with saturated sodium bicarbonate, dry over magnesium sulfate, filter and concentrate in vacuo to yield 3-[(phenacyl)methylamino]-2-carbethoxy-6-nitroindole.

Dissolve 3-[(phenacyl)methylamino]-2-carbethoxy-6-nitroindole 0.3 mmol) in tetrahydrofuran and water. Add lithium hydroxide (0.9 mmol). Stir the reaction at room temperature for 6 hours. Acidify with 1N HCl extract with ethyl acetate and separate the layers. Dry the organic phase over magnesium sulfate, filter and concentrate in vacuo to yield the title compound.

EXAMPLE 5

Preparation of 3-[(Phenacyl)amino]-2-[(2-dimethylamino)-carbethoxy]-6-chloroindole

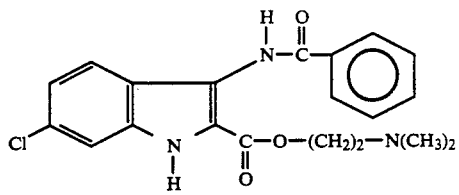

Mix 3-[(phenacyl)amino]-2-carbmethoxy-6-chloroindole (1.0 g, 3.04 mmol) with 2-dimethylaminoethanol (5 mL), potassium carbonate (3.04 mmol) and toluene (25 mL) and warm at 70° C. for 24 hours. Cool and apply to a silica gel column and elute with 5% methanol/chloroform. Evaporate the solvent to 150 mL and add hot hexane (200 mL). Cool and filter to give the title compound as a white powder (700 mg, 64%).

EXAMPLE 6

Preparation of 3-[(Methyloxalylate)amino]-2-carbmethoxy-indole

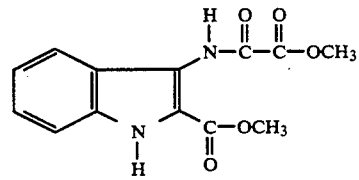

Step a: 2-[(Carbmethoxy)methylamino]-2-benzonitrile

Dissolve 2-aminobenzonitrile (10 g, 85 mmol) in methanol (20 mL). Add sodium hydrogen carbonate (7.6 g, 90 mmol) and methyl bromoacetate (8.5 mL, 90 mmol) and heat at reflux overnight. Cool and filter. Evaporate the solvent in vacuo and purify by flash chromatography (25% ethyl acetate/hexane). Recrystallize (ethyl acetate/hexane) to give the title compound as white crystals; first crop (6 g, 37%) and second crop (3 g, 18%); mp 86°-88° C.

Step b: 3-Amino-2-carmethoxy-indole

Dissolve potassium tert-butoxide (31.5 mmol) in anhydrous tetrahydrofuran (31.5 mL) and cool to 5° C. Add a solution of 2-(carmethoxy)methylaminobenzonitrile (6 g, 31.5 mmol) in anhydrous tetrhydrofuran. Allow to warm to room temperature and stir for 3 hours. Pour into water/ethyl acetate, separate the organic phase and dry (MgSO$_4$). Evaporate the solvent in vacuo and purify by flash chromatography (25% ethyl acetate/hexane) and recrystallize (25% ethyl acetate/hexane then adding hexane until needles appear) to give the title compound; first crop (2.3 g, 38%) and second crop (0.5 g, 8.3%); mp 128°-135° C. (dec).

Step c: 3-[(Methyloxalylate)amino]-2-carbmethoxy-indole

Dissolve 3-amino-2-carbmethoxy-indole (250 mg, 1.31 mmol) in methylene chloride (3 mL). Add triethylamine (182 μL, 1.31 mmol), followed by slow addition of methyl chlorooxalate (120 μL, 1.31 mmol). Stir at

EXAMPLE 7

Preparation of 3-[(Oxalyl)amino]-2-carboxy-indole

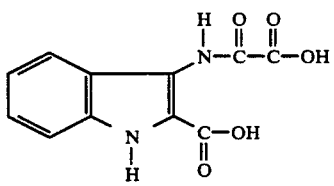

Dissolve 3-[(methyloxalylate)amino]-2-carbmethoxy-indole (200 mg, 0.72 mmol) in methanol (10 mL). Add sodium hydroxide (3.62 mL of a 1N solution in water, 3.62 mmol) and warm to 40° C. for 1 hour. Dilute with water (50 mL), acidify and extract into ethyl acetate. Separate the organic phase, dry (MgSO$_4$) and evaporate the solvent in vacuo to give the title compound as a yellow powder (84%); mp 200°–04° C.

An alternative synthetic procedure for preparing appropriate starting materials for compounds of Formula I is set forth in Scheme V. In Scheme V, all substituents, unless otherwise indicated, are as previously defined.

Scheme V

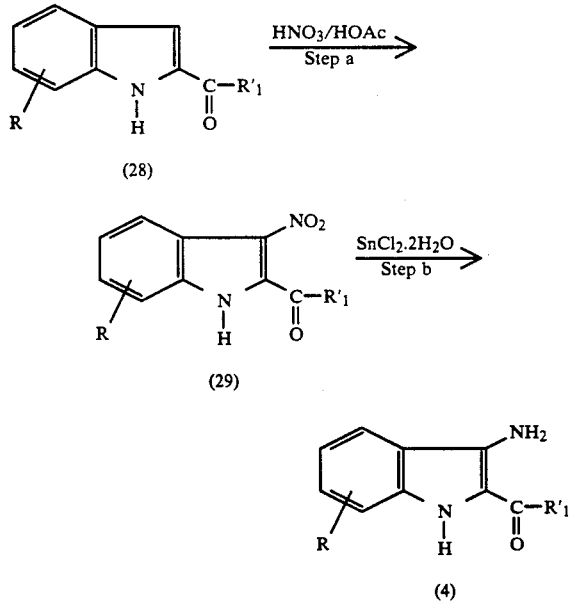

R'$_1$ = OR$_2$

In step a, an appropriate 2-carbalkoxy-indole of structure (28) can be nitrated to produce the 2-carbalkoxy-3-nitro-indole of structure (29).

The nitration reaction of step a can be carried out using techniques known in the art. Typically, the 2-carbalkoxy-indole as described by structure (14) is contacted with a large excess of fuming nitric acid. The reactants are typically contacted in an acidic medium, such as acetic acid. The reactants are typically stirred for a period of time ranging from 10 minutes to 4 days and at a temperature range of from 0° C. to room temperature. The 2-carbalkoxy-3-nitro-indole of structure (29) can be recovered from the reaction by precipitation with water followed by filtration.

In step b, the nitro functionality of the appropriate 2-carbalkoxy-3-nitro-indole of structure (29) can be reduced to the corresponding amino functionality to produce the 3-amino-2-carbalkoxy-indole of structure (4).

The reduction reaction of step b can also be carried out using techniques known in the art. Typically, the 2-carbalkoxy-3-nitro-indole of structure (29) is contacted with 5 equivalents of tin (II) chloride dihydrate. The reactants are typically contacted in an organic solvent such as ethanol. The reactants are typically stirred together for a period of time ranging from 1–24 hours and at a temperature range from about room temperature to reflux. The 3-amino-2-carbalkoxy-indole of structure (4) can be recovered from the reaction by techniques such as flash chromatography.

Compounds of Formula I can be prepared from the appropriate 3-amino-2-carbalkoxy-indole of structure (4) as described previously in Scheme I, steps c–g. Side-chain functionality may also be manipulated as described previously in Scheme I.

Starting materials for use in the general synthetic procedure outling in Scheme V are readily available to one of ordinary skill in the art and described previously in Scheme I.

The following examples present typical syntheses as described in Scheme V. These examples are understood to be illustrative only and are not intended to limit the scope of the present invention in any way.

EXAMPLE 8

Preparation of 3-[(Phenacyl)amino]-2-carbethoxy-4,6-dichloroindole

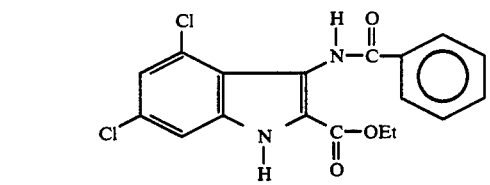

Step a: 3-Nitro-2-carbethoxy-4,6-dichloroindole

Dissolve 3,5-dichlorophenylhydrazine hydrochloride (300 g) in anhydrous ethanol (2 L). Add ethyl pyruvate (153.6 mL) and concentrated sulfuric acid (25 mL). Sir at room temperature under a nitrogen atmosphere for 3 hours. Evaporate the solvent in vacuo, take up the residue in ethyl acetate/water and treat with saturated sodium hydrogen carbonate. Separate the aqueous phase and extract with ethyl acetate. Combine the organic phases, dry (MgSO$_4$) and evaporate the solvent in vacuo to give the 3,5-dichlorophenylhydrazone of ethyl pyruvate and as a solid (371.6 g, 96%). Both E and Z isomers are obtained.

$^1$H NMR (CDCl$_3$), 90 MHz) isomer A, δ 11.9 (b, 1H), 7.0 (d, 2H), 6.8 (d, 1H), 4.2 (q, 2H), 2.1 (s, 3H), 1.3 (t, 3H); isomer B δ 7.9 (b, 1H), 7.2–6.8 (m, 3H), 4.3 (q, 2H), 2.1 (s, 3H), 1.4 (t, 3H).

Add polyphosphoric acid (2 kg) to the 3,5-dichlorophenylhydrazone of ethyl pyruvate (100 g) and heat on a steam bath for 5 hours. Add a small amount of ice and pour onto ice to decompose the polyphosphoric acid. Extract the resulting suspension into ethyl acetate (3×1 L) and dry (MgSO$_4$). Evaporate the solvent in vacuo to give a light brown solid. Stir the solid with ethyl ether (1 L) for 1 hour and filter off 2-carboxyethyl-4,6-dichloroindole. Heat the filtrate with activated charcoal, filter through Celite and evaporate the solvent in vacuo to give a second crop of 2-carboxyethyl-4,6-dichloroindole as a tan solid (89.4 g total, 95%).

IR (KBr) 3406, 3314, 1698, 1568, 1324, 1244, 1214, 840, and 770 cm$^{-1}$.

$^1$H-NMR (DMSO-d$_6$, 300 MHz) δ 12.4 (b, 1H), 7.5 (s, 1H), 7.3 (s, 1H), 7.1 (s, 1H), 4.4 (q, 2H, J=7 Hz), 1.4 (t, 3H, J=7 Hz); 13C-NMR (DMSO-d$_6$, 75 MHz) δ 160.6, 137.6, 129.2, 129.1, 126.9, 124.3, 120.0, 111.4, 105.3, 61.0, 14.2; MS (CI/CH$_4$) m/z 258 (M+H)$^+$.

Anal. Calcd for C$_{11}$H$_9$C$_{12}$NO$_2$: C, 51.19; H, 3.51; N, 5.43; Found: C, 51.38, H, 3.42; N, 5.53.

Mix 2-carboxyethyl-4,6-dichloroindole (50 g) and acetic acid (1 L) and add, by dropwise addition, 90% (white fuming) nitric acid (250 mL). Apply a water bath as necessary to keep the temperature below 29° C. Stir for 10 minutes after all of the solid is dissolved and pour into ice (6 L). Filter off the solid and wash with water. Dissolve the solid in ethyl acetate, treat with saturated sodium hydrogen carbonate solution, and separate the organic phase. Dry (MgSO$_4$), filter and evaporate the solvent in vacuo to give the crude product as a tan solid. Slurry the solid in a small amount of chloroform, filter and dry to give the title compound (36.9 g, δ 3%).

Step b: 3-Amino-2-carbethoxy-4,6-dichloroindole

Dissolve 3-nitro-2-carbethoxy-4,6-dichloroindole (38.1 g) in ethanol (1 L) and add tin (II) chloride dehydrate (163 g). Warm to between 65° and 65° C. for 4 to 5 hours. Cool to room temperature and pour into a mixture of ethyl acetate (3 L) and water (2 L). Add solid potassium carbonate and stir occasionally until the carbon dioxide evolution ceases. Filter throught Celite and separate the organic phase of the filtrate. Dry (MgSO$_4$) and evaporate the solvent in vacuo to give the title compound as an off-yellow solid (33.5 g, 97.6%).

Scheme I, step c:
3-[(Phenacyl)amino]-2-carbethoxy-4,6-dichloroindole

Dissolve 3-amino-2-carbethoxy-4,6-dichloroindole (7.8 g, 27.8 mmol) in methylene chloride (500 mL) and add triethylamine (4.2 mL, 30 mmol) followed by benzoyl chloride (3.5 mL, 30 mmol). Stir at room temperature overnight. Dilute with ethyl acetate (300 mL), wash with water and separate the organic phase. Dry (MgSO$_4$) and evaporate the solvent in vacuo to give a solid. Recrystallize (ethyl acetate) to give the title compound as off-white needles (7.75 g, 74%).

EXAMPLE 9

Preparation of
3-[Phenacyl)amino]-2-carboxy-4,6-dichloroindole

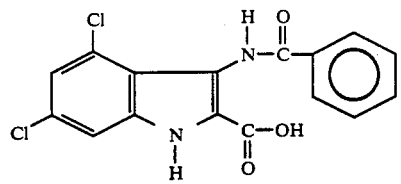

Mix 3-[(phenacyl)amino]-2-carbethoxy-4,6-dichloroindole (300 mg, 0.79 mmol), lithium hydroxide monohydrate (2.39 mmol), tetrahydrofuran (2 mL) and water (2 mL). Stir at room temperature overnight. Dilute with water and ethyl acetate. Acidify the aqueous phase and separate the organic phase. Dry (MgSO$_4$), evaporate the solvent in vacuo, and recrystallize the residue (ethyl acetate/hexane) to give the title compound (175 mg, 64%).

EXAMPLE 10

Preparation of
3-[(Phenacyl)methylamino]-2-carbethoxy-4,6-dichloroindole

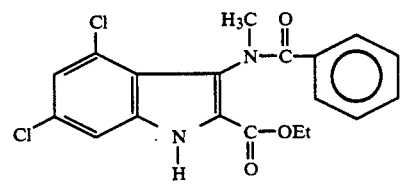

Scheme I, step d$_2$:
3-[(Phenacyl)amino]-2-carbethoxy-4,6-dichloro-1-(tert-butyloxycarbonyl)-indole Mix 3-[(phenacyl)amino)]-2-carbethoxy-4,6-dichloroindole (6 g, 16 mmol), di-tert-butyl dicarbonate (3.5 g, 16 mmol), tetrahydrofuran (90 mL) and dimethylaminopyridine (85 mg, 0.8 mmol) and stir at room temperature for 1 hour. Dilute with ethyl acetate, wash with water and separate the organic phase. Dry (MgSO$_4$) and evaporate the solvent in vacuo. Recrystallize the residue (ethyl acetate/hexane) to give the title compound as white crystals (7.0 g, 92%); mp 143°-4° C.

Scheme I, step e:
3-[(Phenacyl)methylamino]-2-carbethoxy-4,6-dichloro-1-(tert-butyloxycarbonyl)-indole Suspend sodium hydride (20 mg of a 60% dispersion, 0.5 mmol) in anhydrous tetrahydrofuran (1 mL) and cool to 0° C. under a nitrogen atmosphere. Slowly add 3-[(phenacyl)amino]-2-carbethoxy-4,6-dichloro-1-(tert-butyloxycarbonyl)-indole (220 mg, 0.46 mmol) in tetrahydrofuran (1 mL). Stir at 0° C. for 0.5 hours. Add methyl iodide (31 uL, 0.5 mmol) and stir at 0° C. for 2 hours. Quench with water, extract into ethyl acetate and separate the organic phase. Dry (MgSO$_4$) and evaporate the solvent in vacuo. Purify the residue by flash chromatography (25% ethyl acetate/hexane) and recrystallize (hexane) to give the title compound (2.9 g, 95%); mp 130°-1° C.

Scheme I, step f:
3-[(Phenacyl)methylamino]-2-carbethoxy-4,6-dichloroindole

Dissolve 3-[(phenacyl)methylamino]-2-carbethoxy-4,6-dichloro-1-(tert-butyloxycarbonyl)-indole (2.8 g, 5.7 mmol) in methylene chloride (5 mL). Add trifluoroacetic acid (5 mL) and stir for 1 hour. Evaporate to dryness in vacuo and recrystallize the residue (ethyl acetate/hexane) to give the title compound as white needles (1.8 g, 82%); mp 195°–97° C.

EXAMPLE 11

Preparation of 3-[(Phenacyl)methylamino]-2-carboxy-4,6-dichloroindole

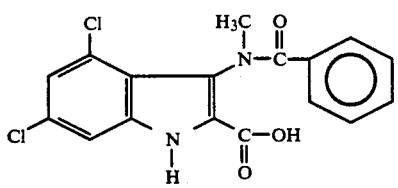

Dissolve 3-[(phenacyl)methylamino]-2-carbethoxy-4,6-dichloroindole (800 mg, 2.04 mmol) in tetrahydrofuran (5 mL) and water (5 mL). Add lithium hydroxide monohydrate (252 mg, 6 mmol) and stir at room temperature overnight. Warm to 50° C. in an water bath for several hours, dilute with water (10 mL) and ethyl acetate (25 mL). Stir and acidify with 1N hydrochloric acid. Separate the organic phase and dry. Evaporate the solvent in vacuo and recrystallize (ethyl acetate/hexane) to give the title compound as a white powder (630 mg, 85%); mp 275° C. (dec).

Example 11a

Preparation of 3-[(Phenacyl)methylamino]-2-tetrazole-4,6-dichloroindole

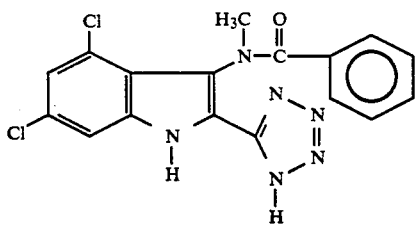

Scheme II, step a: Suspend 3-[(Phenacyl)methylamino]-2-carboxy-4,6-dichloroindole(4.25 mmol) in toluene (5 mL), add thionyl chloride (5 mL) and reflux for 1.5 hours. Concentrate the reaction in vacuo and reconcentrate two more times from toluene. Place under high vacuum for 1 hour. Dissolve the acid chloride in toluene (5 mL) and add excess t-butylamine. Stir the reaction at room temperture. Dilute the reaction with ethyl acetate and wash with 1M HCl (3×100 mL), dry over magnesium sulfate, filter and concentrate in vacuo yield the tert-butylamide.

Scheme II, step b: Dissolve the above tert-butylamide derivative (3.26 mmol) in methylene chloride and add trifluoroacetic anhydride (32.7 mmol). Stir the reaction at room temperature for 6 hours under a nitrogen atmosphere. Rinse the reaction with saturated sodium bicarbonate, water and concentrate in vacuo to yield the 2-cyanoindolyl derivative.

Scheme III, step c: Dissolve the above 2-cyanoindolyl derivative (3 mmol) in N-methylpyrrolidinone (5 mL) and treat with tributyltin chloride (3.24 mmol), sodium azide (3 mmol) and heat to 70° C. for 3 days. Dilute the reaction with an additional amount of N-methylpyrrolidinone (5 mL) and allow to cool. Add 1N HCl (5 mL) and extract with ethyl acetate. Dry the organic phase over sodium sulfate, filter and concentrate in vacuo to yield the title compound.

Example 11b

Preparation of 3-[(tetrazoleacyl)amino]-2-carboxy-4,6-dichloroindole

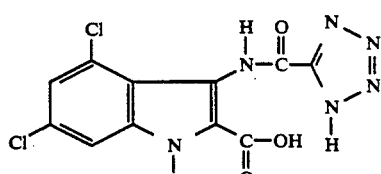

Scheme III, step a: Combine 3-amino-2-carb-tert-butoxy-4,6-dichloroindole (5 mmol), triethylamine (5.5 mmol) and methylene chloride (100 mL). Add methyl oxalyl chloride (5.5 mmol) and stir at room temperature for 4 hours. Pour the reaction into saturated sodium bicarbonate and separate the layers. Wash the organic phase with saturated sodium chloride, dry over magnesium sulfate, filter and concentrate in vacuo to yield the 3-amidoindolyl derivative.

Scheme III, step d: Dissolve the above aminoindolyl derivative (3.2 mmol) in tetrahydrofuran and water (1:1) and treat with lithium hydroxide (3.2 mmol). Stir the reaction for 6 hours, carefully acidify to pH 5 and immediately extract the aqueous with ethyl acetate. Dry the organic phase with magnesium sulfate, filter and concentrate in vacuo to yield the monoacid.

Scheme III, step e: Dissolve the above monoacid (3 mmol) in tetrahydrofuran and treat with triphenyphosphine (3 mmol), diethylazodicarboxylate (3 mmol) followed by N-hydroxysuccinimide at room temperature. Stir for 1 hour and then treat the reaction with tert-butylamine (3 mmol). Stir for an additional 2 hours at room temperature and dilute with water. Extract the aqueous with ethyl acetate, dry the organic phase over magnesium sulfate, filter and concentrate in vacuo to afford the tert-butylamide derivative.

Scheme III, step f: Dissolve the above tert-butylamide derivative (3 mmol) in methylene chloride and add trifluoroacetic anhydride (30 mmol). Stir the reaction at room temperature for 6 hours under a nitrogen atmosphere. Rinse the reaction with saturated sodium bicarbonate, water and concentrate in vacuo yield the cyano derivative.

Scheme III, step g: Dissolve the above cyano derivative (3 mmol) in N-methylpyrrolidinone (5 mL) and treat with tributyltin chloride (3.24 mmol), sodium azide (3 mmol) and heat to 7020 C. for 3 days. Dilute the reaction with an addtional amount of N-methylpyrrolidinone (5 mL) and allow to cool. Add 1N HCl (5 mL) and extract with ethyl acetate. Dry the organic phase over sodium sulfate, filter and concentrate in vacuo to yield the tetrazole derivative.

Scheme III, step h: Dissolve the above tetrazole derivative (3 mmol) in methylene chloride (20 mL). Add trifluoroacetic acid (2 mL) and stir at room temperature for 3 hours. Dilute the reation with water (20 mL) and separate the layers. Dry the organic phase over magnesium sulfate, filter and concentrate in vacuo to yield the title compound.

Example 11c

Preparation of
3-[(tetrazoleacyl)amino]-2-carbotetrazole-4,6-dichloroindole

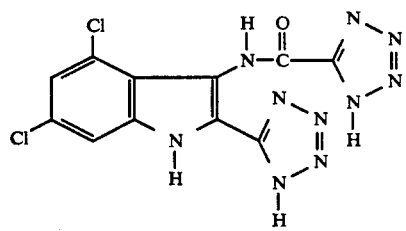

Scheme III, step e: Suspend 3-[(tetrazoleacyl)amino]-2-carboxy-4,6-dichloroindole (3 mmol) in toluene (5 mL), add thionyl chloride (5 mL) and reflux for 1.5 hours. Concentrate the reaction in vacuo and reconcentrate two more times from toluene. Place under high vacuum for 1 hour. Dissolve the acid chloride in toluene (5 mL) and add excess t-butylamine. Stir the reaction at room temperture. Dilute the reaction with ethyl acetate and wash with 1M HCl (3×100 mL), dry over magnesium sulfate, filter and concentrate in vacuo yield the tert-butylamide.

Scheme III, step f: Dissolve the above tert-butylamide derivative (3 mmol) in methylene chloride and add trifluoroacetic anhydride (30 mmol). Stir the reaction at room temperature for 6 hours under a nitrogen atmosphere. Rinse the reaction with saturated sodium bicarbonate, water and concentrate in vacuo yield the 2-cyanoindolyl derivative.

Scheme III, step g: Dissolve the above 2-cyanoindolyl derivative (3 mmol) in N-methylpyrrolidinone (5 mL) and treat with tributyltin chloride (3.24 mmol), sodium azide (3 mmol) and heat to 150° C. for 4 hours. Dilute the reaction with an addtional amount of N-methylpyrrolidinone (5 mL) and allow to cool. Add 1N HCl (5 mL) and extract with ethyl acetate. Dry the organic phase over sodium sulfate, filter and concentrate in vacuo to yield the title compound.

EXAMPLE 12

Preparation of
3-[(Phenacyl)methylamino]-2-sodium-carboxylate-4,6-dichloroindole

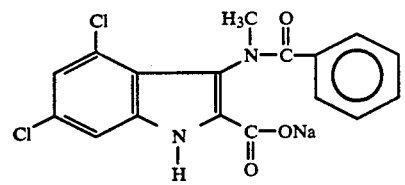

Suspend 3-[(phenacyl)methylamino]-2-carboxy-4,6-dichloroindole (0.98 g, 2.7 mmol) in water and add sodium hydroxide (11 mL of a 0.25M solution) and heat the partial solution until a pale yellow solution is obtained. Filter and freeze-dry to give the title compound (1.01 g, 97.3%) as a white powder.

Anal. Calcd for $C_{17}H_{11}C_{12}N_2O_3 \cdot H_2O \cdot Na$: C, 50.64; H, 3.25; N, 6.95; Found: C, 50.75; H, 2.93; N, 6.86.

EXAMPLE 13

Preparation of
3-[(Phenacyl)methylamino]-2-[(2-dimethylamino)-carbethoxy]-4,6-dichloroindole

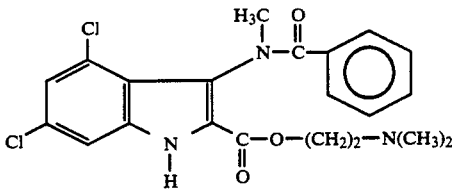

Mix 3-[(phenacyl)amino]-2-carbethoxy-4,6-dichloroindole (1 g, 2.56 mmol), 2-dimethylaminoethanol (5 mL), potassium carbonate (353 mg, 2.56 mmol) and toluene (15 mL). Heat at 70° C. overnight. Purify by flash chromatography (5% methanol/chloroform) and recrystalize (ethyl acetate/hexane) to give the title compound (600 mg, 54%); mp 171°-2° C.

EXAMPLE 14

Preparation of
3-[(Phenacyl)ethylamino]-2-carbethoxy-4,6-dichloroindole

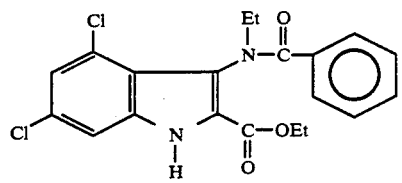

Scheme I, step e:
3-[(Phenacyl)ethylamino]-2-carbethoxy-4,6-dichloro-1-tert-butyloxycarbonyl-indole Suspend sodium hydride (52 mg of a 60% dispersion, 1.73 mmol) in anhydrous dimethylformamide and cool to −10° C. Add, by dropwise addition, a solution of 3-[(phenacyl)amino]-2-carbethoxy-4,6-dichloro-1-tert-butyloxycarbonyl-indole (0.75 g, 1.57 mmol) in dimethylformamide. Stir under a nitrogen atmosphere for 30 minutes. Add ethyl iodide (0.27 g, 1.73 mmol) and stir at −10° C. for 5 hours. Pour into 1N hydrochloric acid (100 mL) and extract into ethyl acetate. Separate the organic phase and dry (MgSO4). Evaporate the solvent in vacuo and purify by flash chromatography (4:1 methylene chloride/ethyl acetate and recrystallize (ethyl acetate/hexane) to give the title compound; mp 110°-11° C.

Scheme I, step f:
3-[(Phenacyl)ethylamino]-2-carbethoxy-4,6-dichloroindole

Dissolve 3-[(phenacyl)ethylamino]-2-carbethoxy-4,6-dichloro-1-tert-butyloxycarbonyl-indole (0.79 g, 1.57 mmol) in methylene chloride (5 mL) and add, by dropwise addition, trifluoroacetic acid (5 mL). Stir for 4 hours and pour carefully into saturated sodium hydrogen carbonate (100 mL). Extract into ethyl acetate, dry (MgSO4) and evaporate the solvent in vacuo to give as yellow oil. Recrystallize (ethyl acetate/hexane) to give the title compound (0.23 g, 36%); mp 203°-5° C.

EXAMPLE 15

Preparation of 3-[(Phenacyl)ethylamino]-2-carboxy-4,6-dichloroindole

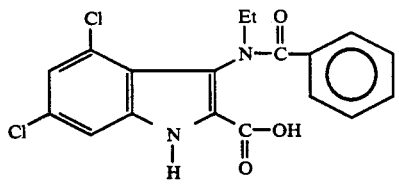

Mix 3-[(phenacyl)ethylamino]-2-carbethoxy-4,6-dichloroindole (600 mg, 1.48 mmol), water (10 mL) and tetrahydrofuran (10 mL). Add lithium hydroxide monohydrate (0.22 g, 5.18 mmol) and stir at room temperature for 24 hours. Heat to reflux for 5 hours then pour into 1N hydrochloric acid (100 mL). Extract into ethyl acetate, dry (MgSO4) and evaporate the solvent in vacuo to give the crude product (0.72 g) as a white solid. Recrystallize (ethyl acetate/hexane) to give the title compound (0.32 g, 57%); mp 254°-6° C.

EXAMPLE 16

Preparation of 3-[(Phenacyl)benzylamino]-2-carbethoxy-4,6-dichloroindole

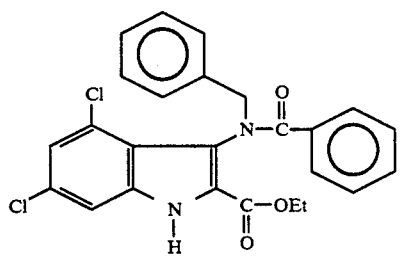

Scheme I, step e: 3-[(Phenacyl)benzylamino]-2-carbethoxy-4,6-dichloro-1-tert-butyloxycarbonyl-indole Suspend sodium hydride (42 mg of a 60% dispersion, 1.39 mmol) in dimethylformamide, place under nitrogen atmosphere and cool to −10° C. Add, by dropwise addition, a solution of 3-[(phenacyl)amino]-2-carbethoxy-4,6-dichloro-1-tert-butyloxycarbonyl-indole (0.6 g, 1.26 mmol) in dimethylformamide. Stir at −10° C. for 30 minutes and add, by dropwise addition, benzyl bromide (0.24 g, 1.39 mmol). Stir for 5 hours, pour into 1N hydrochloric acid and extract into ethyl acetate. Dry (MgSO4) and evaporate the solvent in vacuo to give the title compound as a yellow oil.

Scheme I, step f: 3-[(Phenacyl)benzylamino]-2-carbethoxy-4,6-dichloroindole

Dissolve 3-[(phenacyl)benzylamino]-2-carbethoxy-2,6-dichloro-1-tert-butyloxycarbonyl-indole (0.68 g, 1.26 mmol) in methylene chloride (5 mL) and add, by dropwise addition, trifluoroacetic acid (5 mL). Stir for 4 hours then slowly add to saturated sodium hydrogen carbonate (100 mL). Extract into methylene chloride, dry (MgSO4) and evaporate the solvent in vacuo. Recrystallize (ethyl acetate/hexane) to give the title compound (0.34 g, 59%); mp 174°-5° C.

EXAMPLE 17

Preparation of 3-[(Phenacyl)benzylamino]-2-carboxy-4,6-dichloroindole

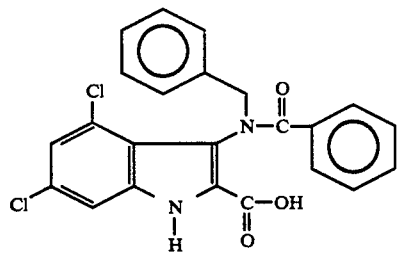

Dissolve 3-[(phenacyl)benzylamino]-2-carbethoxy-4,6-dichloroindole (0.5 g, 1.07 mmol) in tetrahydrofuran (10 mL) and water (10 mL). Add lithium hydroxide monohydrate (0.16 g, 3.74 mmol) and stir for 24 hours. Heat at reflux for 6 hours and pour into 1N hydrochloric acid (100 mL). Extract into ethyl acetate, dry (MgSO4) and evaporate the solvent in vacuo. Recrystallize (ethyl acetate/hexane) to give the title compound; mp 266°-7° C.

EXAMPLE 18

Preparation of 3-[(Phenacyl)carbethoxymethyl-amino]-2-carbethoxy-4,6-dichloroindole

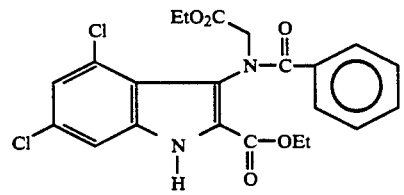

Scheme I, step e: 3-[(Phenacyl)carbethoxymethyl-amino]-2-carbethoxy-4,6-dichloro-1-tert-butyloxycarbonyl-indole Suspend sodium hydride (29.3 mg of a 60% dispersion, 0.976 mmol) in dimethylformamide (2 mL), place under nitrogen atmosphere and cool to 0° C. Add, by dropwise addition, a solution of 3-[(phenacyl)amino]-2-carbethoxy-4,6-dichloro-1-tert-butyloxycarbonyl-indole (0.42 g, 0.887 mmol) in dimethylformamide (3 mL). Stir for 2 hours, dilute with ethyl acetate (100 mL) and wash with 1N hydrochloric acid. Dry (MgSO4) and evaporate the solvent in vacuo to give 0.58 g crude product. Recrystallize (ethyl acetate/hexane) to give the title compound (0.36 g, 72%); mp 129°-30° C.

Scheme I, step f: 3-[(Phenacyl)carbethoxymethyl-amino]-2-carbethoxy-4,6-dichloroindole Dissolve 3-[(phenacyl)carbethoxymethyl-amino]-2-carbethoxy-4,6-dichloro-1-tert-butyloxycarbonyl-indole (0.4 g, 0.71 mmol) in methylene chloride (6 mL) and add, by dropwise addition, trifluoroacetic acid (6 mL). Stir for 3.5 hours and pour slowly into saturated sodium hydrogen carbonate (100 mL). Extract with ethyl acetate and dry (MgSO4). Evaporate the solvent in vacuo and recrystallize the residue (ethyl acetate/hexane) to give the title compound (0.28 g, 85%); mp 139°–40° C.

EXAMPLE 19

Preparation of 3-[(Phenacyl)carboxymethyl-amino]-2-carboxy-4,6-dichloroindole

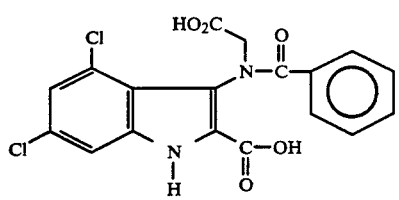

Dissolve 3-[(phenacyl)carbethoxymethyl-amino]-2-carbethoxy-4,6-dichloroindole (0.29 g, 0.626 mmol) in tetrahydrofuran (27 mL) and water (13 mL). Add lithium hydroxide monohydrate (0.158 g, 3.76 mmol) and stir overnight. Pour into 1N hydrchloric acid (100 mL) and extract into ethyl acetate. Dry (MgSO4) and evaporate the solvent in vacuo. Recrystallize (ethyl acetate/hexane) to give the title compound (0.15 g, mp 235°–7° C.

EXAMPLE 20

Preparation of 3-[(2-Benzylphenacyl)amino]-2-carbethoxy-4,6-dichloroindole

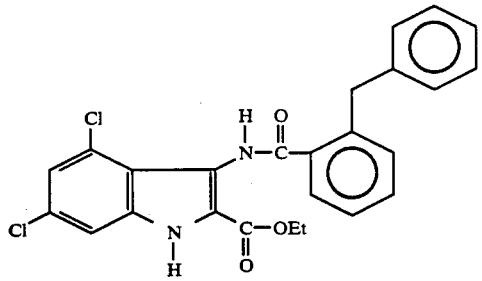

Mix 3-amino-2-carbethoxy-2,6-dichloroindole (2.73 g, 10 mmol), 2-benzyl benzoyl chloride (10 mmol) in pyridine (50 mL) and heat at 60° C. for 48 hours. Pour into water, separate the organic phase and wash with 1N hydrochloric acid, then with saturated sodium hydrogen carbonate. Dry (MgSO4) and evaporate the solvent in vacuo. Purify by flash chromatography (25% ethyl acetate/hexane) and recrystallize (ethyl acetate/hexane) to give the title compound (450 mg); mp 225°–227° C.

Anal. Calcd for C25H20Cl2N2O3: C, 64.25; H, 4.31; N, 5.99; Found: C, 63.91; H, 4.42; N, 6.12.

EXAMPLE 21

Preparation of 3-[(2-Benzylphenacyl)amino]-2-carboxy-4,6-dichloroindole

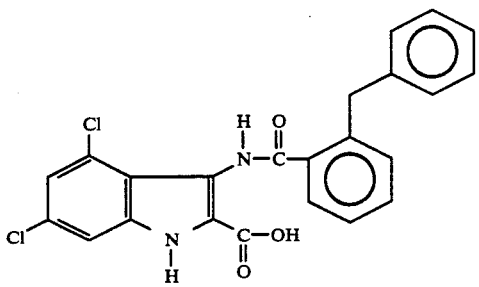

Dissolve 3-[(2-benzylphenacyl)amino]-2-carbethoxy-4,6-dichloroindole (100 mg, 0.214 mmol) in tetrahydrofuran (7 mL) and water (7 mL). Add lithium hydroxide monohydrate (25.2 mg, 6 mmol) and stir overnight. Stir at 40° C. for 2 hours, dilute with water (10 mL) and ethyl acetate (25 mL). Acidify with 1N hydrochloric acid while stirring. Separate the organic phase, dry (MgSO4) and evaporate the solvent in vacuo. Recrystallize (ether/hexane) to give the title compound (89 mg, 95%); mp 234°–235° C.

Anal. Caldc for C23H16Cl2N2O3: C, 62.88; H, 3.67; N, 6.38; Found: C, 63.04; H, 4.05; N, 5.97.

EXAMPLE 22

Preparation of 3-[(2-Benzylphenacyl)methylamino]-2-carbethoxy-4,6-dichloroindole

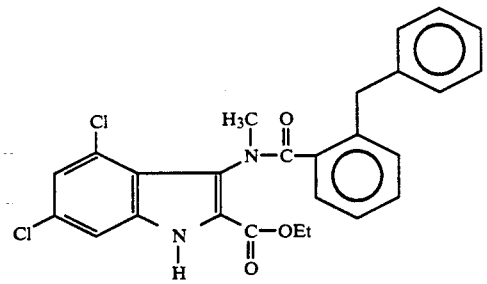

Scheme I, step d2: 3-[(2-Benzylphenacyl) amino]-2-carbethoxy-4,6-dichloro-1-tert-butyloxycarbonyl-indole Dissolve 3-[(2-benzylphenacyl)amino]-2-carbethoxy-4,6-dichlorocarbonylindole (400 mg, 0.856 mmol) in tetrahydrofuran (40 mL). Add di-tert-butyl dicarbonate (0.9 mmol) and dimethylaminopyridine (10 mg). Stir for 2 hours and partition between ethyl acetate and water. Separate the organic phase, dry (MgSO4) and evaporate the solvent in vacuo. Recrystallize (ethyl acetate/hexane) to give the title compound (420 mg, 86%) as a white solid; mp 163° C.

Scheme I, step e: 3-[(2-Benzylphenacyl)methylamino]-2-carbethoxy-4,6-dichloro-1-tert-butyloxycarbonyl-indole Suspend sodium hydride (32 mg of a 60% dispersion, 0.8 mmol) in anhydrous dimethylformamide (1 mL).

Add, by dropwise addition, a solution of 3-[(2-benzyl-phenacyl)amino]-2-carbethoxy-4,6-dichloro-1-tert-butyloxycarbonyl-indole (430 mg, 0.76 mmol) in dimethylformamide (2 mL). Stir at room temperature for 15 minutes. Add methyl iodide (49.5 uL, 0.8 mmol) and stir for 2 hours. Quench with water, extract into ethyl acetate, wash with water and dry. Evaporate the solvent in vacuo and purify by flash chromatography (25% ethyl acetate/hexane) to give the title compound. Anal. Calcd for $C_{31}H_{28}Cl_2N_2O_5$: C, 64.25; H, 4.87; N, 4.83; Found: C, 63.95; H, 5.26; N, 4.86.

Scheme I, step f:
3-[(2-Benzylphenacyl)methylamino]-2-carbethoxy-4,6-dichloroindole Dissolve 3-[(2-benzylphenacyl)methylamino]-2-carbethoxy-4,6-dichloro-1-tert-butyloxycarbonyl-indole (320 mg, 0.55 mmol) in methylene chloride (5 mL). Add trifluoroacetic acid (1 mL) and stir at room temperature for 3 hours. Evaporate the solvent in vacuo and recrystallize (ethyl acetate/hexane) to give the title compound (250 mg, 95%); mp 208°–209° C.

EXAMPLE 23

Preparation of
3-[(2-Benzylphenacyl)methylamino]-2-carboxy-4,6-dichloroindole

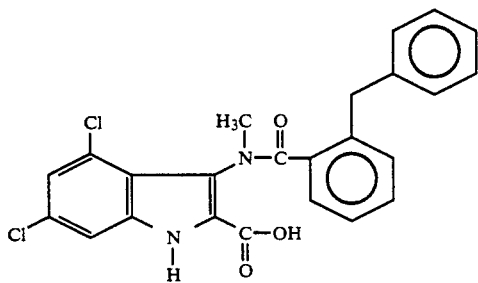

Dissolve 3-[(2-benzylphenacyl)methylamino]-2-carbethoxy-4,6-dichloroindole (200 mg, 0.41 mmol) in tetrahydrofuran (3 mL) and add water (3 mL). Add lithium hydroxide monohydrate (1.2 mmol) and heat at 60° C. overnight. Add addition lithium hydroxide monohydrate (1.2 mmol) and heat at 60° C. for 5 hours. Allow some of the tetrahydrofuran to evaporate and add methanol to form a homogeneous solution. Heat for 3 days, adding additional lithium hydroxide monohydrate (2.4 mmol). Dilute with water and filter. Acidify, extract into ethyl acetate and dry (MgSO4). Evaporate the solvent in vacuo and recrystallize (ethyl acetate/hexane) to give the title compound as a white powder (180 mg, 97%); mp 280°–83° C.

Anal. Calcd for $C_{24}H_{18}Cl_2N_2O_3 \cdot 0.33$ ethyl acetate: C, 63.04; H, 4.31; N, 5.81; Found: C, 62.76; H, 4.41; N, 5.65.

EXAMPLE 24

Preparation of
3-[(3-Pyridacyl)amino]-2-carbethoxy-4,6-dichloroindole

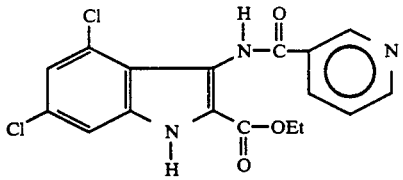

Mix 3-amino-2-carbethoxy-4,6-dichloroindole (7 g, 25.6 mmol), nicotinyl chloride hydrochloride (5 g, 28 mmol), dimethylaminopyridine (200 mg) and pyridine (70 mL) and stir for 2 days at room temperature. Pour into water, filter the white solid and recrystallize (ethyl acetate/methanol) to give the title compound (5.65 g, 58%); mp 247°–48° C.

EXAMPLE 25

Preparation of
3-[(3-Pyridacyl)amino]-2-carboxy-4,6-dichloroindole

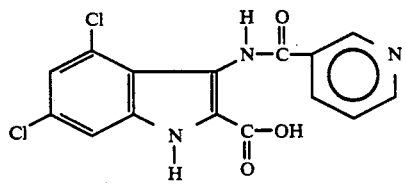

Mix 3-[[pyridacyl)amino]-2-carbethoxy-4,6-dichloroindole (390 mg, 1.03 mmol), lithium hydroxide monohydrate (3 mmol), tetrahydrofuran (10 mL) and water (10 mL). Stir overnight at room temperature. Dilute with ethyl acetate and water, separate the aqueous phase and acidify to pH 3. Filter the precipitate and dry under vacuum to give the title compound; mp 285°–90° C. (dec).

EXAMPLE 26

Preparation of
3-[(3-Pyridacyl)methylamino]-2-carbethoxy-4,6-dichloroindole

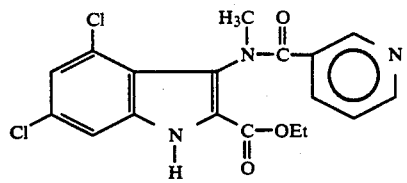

Scheme I, step d2:
3-[(Pyridacyl)amino]-2-carbethoxy-4,6-dichloro-1-tert-butyloxycarbonyl-indole Suspend 3-[(pyridacyl)amino]-2-carbethoxy-2,6-dichloroindole (5.67 g, 15 mmol) in tetrahydrofuran (150 mL). Add di-tert-butyl dicarbonate (3.5 g, 16 mmol) and dimethylaminopyridine (85 mg, 0.8 mmol). Stir at room temperature for 3 hours. Evaporate the solvent in vacuo to a volume of 50 mL and dilute with ethyl acetate (100 mL) and hexane (150 mL). Filter to give the title compound; first crop (4.9 g, 69%) and second crop (1.4 g, 20%).

Scheme I, step e:
3-[(Pyridacyl)methylamino]-2-carbethoxy-4,6-dichloro-1-tert-butyloxycarbonyl-indole Suspend sodium hydride (3.4 mmol) in anhydrous tetrahydrofuran (5 mL) and cool to 0° C. Add, by dropwise addition, a solution of 3-[(pyridacyl)amino]-2-carbethoxy-4,6-dichloro-1-tert-butyloxycarbonyl-indole (1.5 g, 3.1 mmol) in tetrahydrofuran (25 mL). Stir ½ hour, then add methyl iodide (3.4 mmol) and stir at room temperature overnight. Dilute with ethyl acetate and water, separate the organic phase and dry (MgSO₄). Evaporate the solvent in vacuo and purify by flash chromatography (50% ethyl acetate/hexane) to give the title compound (1.4 g, 91%).

Scheme I, step f:
3-[(Pyridacyl)methylamino]-2-carbethoxy-4,6-dichloroindole

Mix 3-[(pyridacyl)methylamino]-2-carbethoxy-4,6-dichloro-1-tert-butyloxycarbonyl-indole (1.2 g, 2.44 mmol), trifluroracetic acid (3 mL) and methylene chloride (3 mL). Stir at room temperature for several hours. Evaporate the solvent in vacuo, dissolve in ethyl acetate, wash with saturated sodium hydrogen carbonate and saturated sodium chloride. Separate the organic phase and dry (MgSO₄). Evaporate the solvent in vacuo and purify by flash chromatography (50% ethyl acetate/hexane) then recrystallize (ether/hexane) to give the title compound (740 mg, 77%).

EXAMPLE 27

Preparation of
3-[(3-Pyridacyl)methylamino]-2-carboxy-4,6-dichloroindole

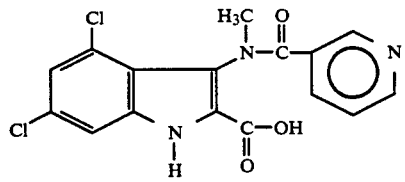

Dissolve 3-[(pyridacyl)methylamino]-2-carbethoxy-4,6-dichloroindole (740 mg, 1.9 mmol) in tetrahydrofuran (5 mL) and dilute with water (5 mL). Add lithium hydroxide monohydrate (239 mg, 45.7 mmol) and stir overnight at room temperature. Warm to 50° C. for 2 hours, dilute with water/ethyl acetate and separate the aqueous phase. Acidify to pH 6 and filter the precipitate. Dry at 70° C. under vacuum for 48 hours to give the title compound as a white powder (611 mg, 88%).

EXAMPLE 28

Preparation of
3-[(3-Pyridacyl)methylamino]-2-sodium-carboxylate-4,6-dichloroindole

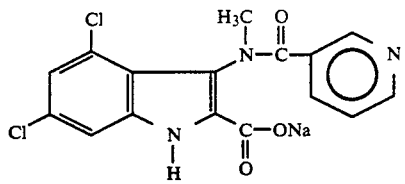

Suspend 3-[(3-pyridacyl)methylamino]-2-carboxy-4,6-dichloroindole (110 mg, 0.3 mmol) in water (10 mL) and add sodium hydroxide (1.2 mL of a 0.25M solution). Warm until a solution was obtained. Filter and freeze-dry to give the title compound (120 mg, 97%).

Example 28a

Preparation of
3-[(p-fluorophenacyl)amino]-2-carbethoxy-4,6-dichloroindole

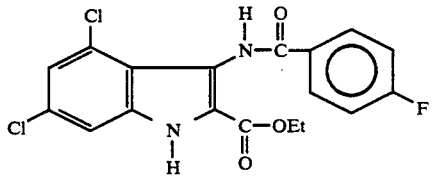

Dissolve 3-amino-2-carbethoxy-4,6-dichloroindole (2.0 g, 7.13 mmol) in methylene chloride (125 mL) and add p-fluorobenzoyl chloride (0.886 mL, 7.5 mmol) followed by triethylamine (1.05 mL, 7.5 mmol). Stir the reaction at room temperature overnight. Add an additional amount of p-fluorobenzoyl chloride (0.20 mL) and triethylamine (0.20 mL) and stir for 6 hours. Dilute the reaction with ethyl acetate, wash with 1N HCl, saturated sodium bicarbonate, saturated sodium chloride, dry over magnesium sulfate, filter and concentrate, in vacuo give a solid. Dissolve the solid in hot ethyl acetate (250 mL), reduce to 200 mL and add hot hexane (50 mL). Cool the solution and collect to resulting solid to yield the title compound as fluffy white crystals (1.52 g, 53%); 241°–243° C.
Anal. Calcd for C₁₈H₁₃Cl₂FN₂O₃: C, 54.70; H, 3.31; N, 7.09; Found: C, 54.63; H, 3.39; N, 6.98.

Example 28b

Preparation of
3-[(p-fluorophenacyl)amino]-2-carboxy-4,6-dichloroindole

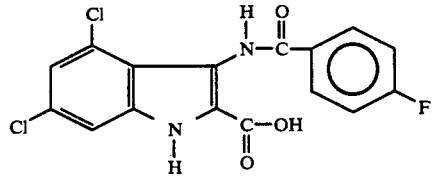

Mix 3-[(p-fluorophenacyl)amino)-2-carbethoxy-4,6-dichloroindole (600 mg, 1.52 mmol), lithium hydroxide (191 mg, 4.55 mmol), tetrahydrofuran (20 mL) and water (20 mL). Stir overnight at room temperature. Dilute with water (20 mL) and ethyl acetate (40 mL). Acidify with 1N HCl while stirring and separate the layers. Dry the organic phase over magnesium sulfate, filter and concentrate in vacuo. Recrystallize the residue (ethyl acetate/hexane) to yield the title compound as a white powder (440 mg, 79%); mp 259°–261° C.

Example 28c

Preparation of 3-[(p-fluorophenacyl)methylamino]-2-carbethoxy-4,6-dichloroindole

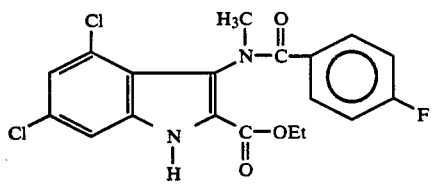

Scheme I, step d₂:
3-(p-fluorophenacyl)amino]-2-carbethoxy-4,6-dichloro-1-(tert-butyloxycarbonyl)-indole Mix 3-[(p-fluorophenacyl)amino]-2-carbethoxy-4,6-dichloroindole (1.5 g, 3.8 mmol), di-tert-butyl dicarbonate (890 mg, 4 mmol), tetrahydrofuran (50 mL), dimethylaminopyridine (42 mg, 0.4 mmol) and stir at room temperture for 1 hour. Concentrate the reaction in vacuo and purify by flash chromatograpy (25% ethyl actetate/hexane) to yield the title compound as a clear oil (1.8 g, 95%).

Scheme I, step e:
3-[(p-fluorophenacyl)methylamino]-2-carbethoxy-4,6-dichloro-1-(tert-butyloxycarbonyl)-indole Suspend sodium hydride (132 mg of a 60% dispersion, 3.3 mmol) in anhydrous tetrahydrofuran (10 mL) and cool to 0° C. under a nitrogen atmosphere. Add 3-[(p-fluorophenacyl)amino]-2-carbethoxy-4,6-dichloro-1-(tert-butyloxycarbonyl)-indole (1.5 g, 3.0 mmol) in tetrahydrofuran (10 mL) dropwise to the suspension. Stir at 0° C. for 30 minutes. Add methyl iodide (0.205 mL, 3.3 mmol) and stir for 30 minutes at 0° C. Warm the reaction to room temperature and quench with water. Extract with ethyl acetate, dry the organic phase over magnesium sulfate, filter and concentrate in vacuo. Purify the residue by flash chromatography (25% ethyl acetate/hexane) to yield the title compound (1.3 g, 85%).

Scheme I, step f:
3-[(p-fluorophenacyl)methylamino]-2-carbethoxy-4,6-dichloroindole Dissolve 3-[(p-fluorophenacyl)methylamino]-2-carbethoxy-4,6-dichloro-1-(tert-butyloxycarbonyl)-indole (1.2 g, 2.35 mmol) in methylene chloride. Add trifluoracetic acid and stir for 2 hours. Concentrate the reaction in vacuo and recrystallize the residue from hot ethyl acetate/hexane to yield the title compound (720 mg, 74%).

Example 28d

Preparation of 3-[(p-fluorophenacyl)methylamino]-2-carboxy-4,6-dichloroindole

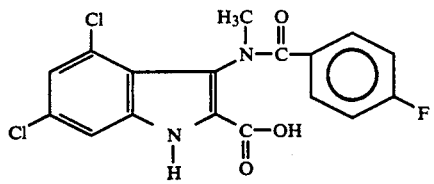

Dissolve 3-[(p-fluorophenacyl)methylamino]-2-carbethoxy-4,6-dichloroindole (660 mg, 1.61 mmol) in tetrahydrofuran (5 mL) and water (5 mL). Add lithium hydroxide (203 mg, 4.8 mmol) and stir for 24 hours at room temperture. Dilute the reaction with water(20 mL) and ethyl acetate (50 mL) and acidify. Separate the layers and dry the organic phase over magnesium sulfate, filter and dilute the filtrate with hexane (100 mL). Recrystallize from this solution to yield the title compound as a white powder (550 mg, 90%).

Anal. Calcd for $C_{17}H_{11}Cl_2FN_2O_3$: C, 53.56; H, 2.91; N, 7.35; Found: C, 53.46; H, 2.90; N, 7.10.

Example 28e

Preparation of 3-[(o-fluorophenacyl)amino]-2-carbethoxy-4,6-dichloroindole

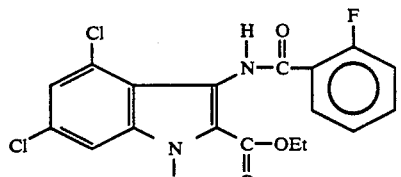

Dissolve 3-amino-2-carbethoxy-4,6-dichloroindole (1.09 g, 4 mmol) in methylene chloride (25 mL) and add triethylamine (0.578 mL, 4 mmol) followed by o-fluorobenzoyl chloride (1 g, 4 mmol). Stir the reaction for 1 hour at room temperature. Add an additional amount of methylene chloride (25 mL) and stir overnight. Dilute the reaction with ethyl acetate (100 mL), wash with water (100 mL) and dry the organic phase. Concentrate in vacuo and recrystallize the residue from ethyl acetate/hexane to yield the title compound (1.05 g, 67%); mp >290° C.

Anal. Calcd for $C_{18}H_{13}Cl_2FN_2O_3$: C, 54.70; H, 3.31; N, 7.09; Found: C, 54.77; H, 3.45; N, 6.79.

Example 28f

Preparation of
3-[(o-fluorophenacyl)methylamino]-2-carbethoxy-4,6-dichloroindole

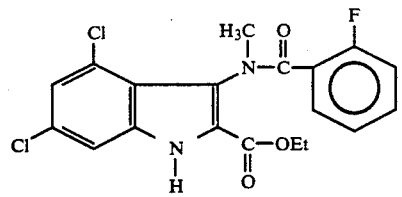

Scheme I, step d₂:
3-[(o-fluorophenacyl)amino]-2-carbethoxy-4,6-dichloro-1-(tert-butyloxycarbonyl)-indole Mix 3-[(o-fluorophenacyl)amino]-2-carbethoxy-4,6-dichloroindole (850 mg, 2.15 mmol), di-tert-butyl dicarbonate (479 mg, 2.5 mmol), tetrahydrofuran (20 mL), dimethylaminopyridine (42 mg, 0.3 mmol) and stir at room temperture for 15 minutes. Dilute with ethyl acetate (100 mL), wash with water, saturated sodium chloride, dry orver magnesium sulfate, filter and concentrate in vacuo. Recrystallize the residue from hot hexane containing some diethyl ether to yield the title compound (880 mg, 84%) as colorless crystals.

Anal. Calck for $C_{23}H_{21}Cl_2FN_2O_5$: C, 55.77; H, 4.27; N, 5.65; Found: C, 55.76; H, 4.47; N, 5.56.

Scheme I, step e:
3-[(o-fluorophenacyl)methylamino]-2-carbethoxy-4,6-dichloro-1-(tert-butyloxycarbonyl)-indole Suspend sodium hydride (80 mg of a 60% dispersion, 2.0 mmol) in anhydrous tetrahydrofuran/dimethylformamide (5 mL/2:1) and cool to 0° C. under a nitrogen atmosphere. Add 3-[(p-fluorophenacyl)amino]-2-carbethoxy-4,6-dichloro-1-(tert-butyloxycarbonyl)-indole (880mg, 1.8 mmol) in tetrahydrofuran/dimethylformamide (20 mL/2:1) dropwise to the suspension. Stir at 0° C. for 30 minutes. Add methyl iodide (0.1244 mL, 2.0 mmol) and stir for 30 minutes at 0° C. Warm the reaction to room temperature and after 4 hours quench with water. Extract with ethyl acetate, wash with saturated sodium chloride, dry over magnesium sulfate, filter and concentrate in vacuo to yield the title compound.

Scheme I, step f:
3-[(o-fluorophenacyl)methylamino]-2-carbethoxy-4,6-dichloroindole Dissolve 3-[(o-fluorophenacyl)methylamino]-2-carbethoxy-4,6-dichloro-1-(tert-butyloxycarbonyl)-indole from above in methylene chloride (5 mL). Add trifluoroacetic acid (3 mL) and stir for 5 hours. Concentrate the reaction in vacuo, dilute with ethyl acetate (100 mL), wash with saturated sodium carbonate, dry over magnesium sulfate, filter and concentrate in vacuo. Recrystallize the residue from ethyl acetate/hexane to yield the title compound (650 mg).

Example 28q

Preparation of
3-[(o-fluorophenacyl)methylamino]-2-carboxy-4,6-dichloroindole

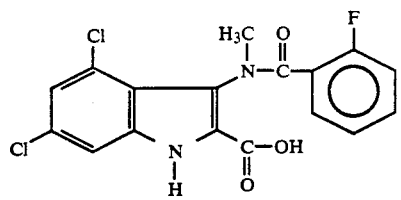

Mix 3-[(o-fluorophenacyl)methylamino]-2-carbethoxy-4,6-dichloroindole (600 mg, 1.47 mmol), lithium hydroxide (184 mg, 4.4 mmol), tetrahydrofuran (10 mL) and water (10 mL). Stir for 24 hours at room temperature. Dilute with ethyl acetate (40 mL). Acidify while stirring and separate the layers. Dry the organic phase over magnesium sulfate, filter and concentrate in vacuo. Recrystallize the residue (ethyl acetate/hexane) to yield the title compound as a white powder (480 mg, 86%).

Anal. Calcd for $C_{17}H_{11}Cl_2FN_2O_3$: C, 53.57; H, 2.91; N, 7.35; Found: C, 53.31; H, 3.05; N, 7.60.

Example 28h

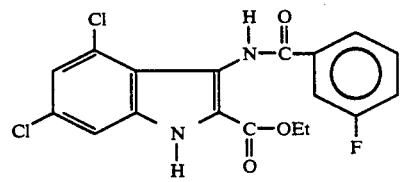

Preparation of
3-((m-fluorophenacyl)amino]-2-carbethoxy-4,6-dichloroindole

Dissolve 3-amino-2-carbethoxy-4,6-dichloroindole (1.09 g, mmol) in methylene chloride (25 mL) and add triethylamine (0.578 mL, 4 mmol) followed by m-fluorobenzoyl chloride (0.488 mL, 4 mmol). Stir the reaction for 1 hour at room temperature. Add an additional amount of methylene chloride (25 mL) and stir overnight. Dilute the reaction with ethyl acetate (100 mL), wash with water (100 mL) and dry the organic phase. Concentrate in vacuo and recrystallize the residue from ethyl acetate/hexane to yield the title compound (1.28 g, 81%); mp 234°-235° C.

Anal. Calcd for $C_{18}H13Cl_2FN_2O_3$: C, 54.70; H, 3.31; N, 7.09; Found: C, 54.58; H, 3.59; N, 7.02.

Example 28i

Preparation of
3-[(m-fluorophenacyl)methylamino]-2-carbethoxy-4,6-dichloroindole

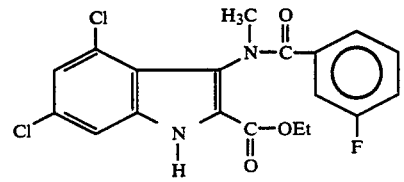

Scheme I, step d₂:
3-[(m-fluorophenacyl)amino]-2-carbethoxy-4,6-dichloro-1-(tert-butyloxycarbonyl)-indole Mix 3-[(m-fluorophenacyl)amino]-2-carbethoxy-4,6-dichloroindole (1.0 g, 2.53 mmol), di-tert-butyl dicarbonate (588 mg, 2.7 mmol), tetrahydrofuran (25 mL), dimethylaminopyridine (42 mg, 0.3 mmol) and stir at room temperture for 15 minutes. Dilute with ethyl acetate (100 mL), wash with water, saturated sodium chloride, dry orver magnesium sulfate, filter and concentrate in vacuo. Recrystallize the residue from hot hexane containing some diethyl ether to yield the title compound (1.1 g, 88%) as colorless crystals.

Anal. Calcd for $C_{23}H_{21}Cl_2FN_2O_5$: C, 55.77; H, 4.27; N, 5.65; Found: C, 55.74; H, 4.56; N, 5.55.

Scheme I, step e:
3-[(m-fluorophenacyl)methylamino]-2-carbethoxy-4,6-dichloro-1-[tert-butyloxycarbonyl)-indole Suspend sodium hydride (97 mg of a 60% dispersion, 2.42 mmol) in anhydrous tetrahydrofuran/dimethylformamide (5 mL/2:1) and cool to 0° C. under a nitrogen atmosphere. Add 3-[(m-fluorophenacyl)amino]- 2-carbethoxy-4,6-dichloro-1-(tert-butyloxycarbonyl)-indole (1.1 g, 2.22 mmol) in tetrahydrofuran/dimethylformamide (20 mL/2:1) dropwise to the suspension. Stir at 0° C. for 30 minutes. Add methyl iodide (0.15 mL, 2.42 mmol) and stir for 30 minutes at 0° C. Warm the reaction to room temperature and after 4 hours quench with water. Extract with ethyl acetate, wash with saturated sodium chloride, dry over magnesium sulfate, filter and concentrate in vacuo to yield the title compound.

Scheme I, step f:
3-[(m-fluorophenacyl)methylamino]-2-carbethoxy-4,6-dichloroindole Dissolve 3-[(m-fluorophenacyl)methylamino]-2-carbethoxy-4,6-dichloro-1-(tert-butyloxycarbonyl)-indole from above in methylene chloride (5 mL). Add trifluoracetic acid (3 mL) and stir for 5 hours. Concentrate the reaction in vacuo, dilute with ethyl acetate (100 mL), wash with saturated sodium carbonate, dry over magnesium sulfate, filter and concentrate in vacuo. Recrystallize the residue from ethyl acetate/hexane to yield the title compound (760 mg).

Example 28j

Preparation of 3-[(m-fluorophenacyl)methylamino]-2-carboxy-4,6-dichloroindole

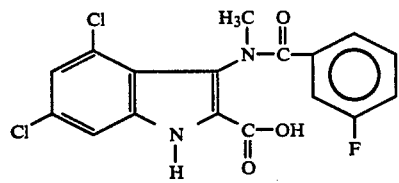

Mix 3-[(m-fluorophenacyl)methylamino]-2-carbethoxy-4,6-dichloroindole (700 mg, 1.7 mmol), lithium hydroxide (210 mg, 5 mmol), tetrahydrofuran (10 mL) and water (10 mL). Stir for 24 hours at room temperature. Dilute with ethyl acetate (40 mL). Acidify while stirring and separate the layers. Dry the organic phase over magnesium sulfate, filter and concentrate in vacuo. Recrystallize the residue (ethyl acetate/hexane) to yield the title compound as a white powder (590 mg, 91%); mp 270°–280° C.

Anal. Calcd for $C_{17}H_{11}Cl_2FN_2O_3$: C, 53.57; H, 2.91; N, 7.35; Found: C, 53.54; H, 3.15; N, 7.24.

Example 28k

Preparation of 3-[(p-trifluoromethylphenacyl)amino]-2-carbethoxy-4,6-dichloroindole

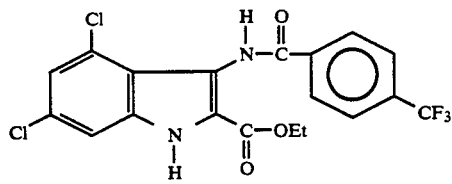

Dissolve 3-amino-2-carbethoxy-4,6-dichloroindole (1.09 g, 4 mmol) in methylene chloride (25 mL) and add triethylamine (0.578 mL, 4 mmol) followed by p-trifluoromethylbenzoyl chloride (0.488 mL, 4 mmol). Stir the reaction for 1 hour at room temperature. Add an additional amount of methylene chloride (25 mL) and stir overnight. Dilute the reaction with ethyl acetate (100 mL), wash with water (100 mL) and dry the organic phase. Concentrate in vacuo and recrystallize the residue from ethyl acetate/hexane to yield the title compound as a white fluffy solid (1.42 g, 80%); mp 250°–252° C.

Anal. Calcd for $C_{19}H_{13}Cl_2F_3N_2O_3$: C, 51.26; H, 2.94; N, 6.29; Found: C, 51.51; H, 3.17; N, 6.59.

Example 28l

Preparation of 3-[(p-trifluoromethylphenacyl)methylamino]-2-carbethoxy-4,6-dichloroindole

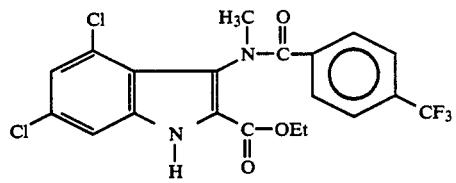

Scheme I, step d₂:
3-[(p-trifluoromethylphenacyl)amino]-2-carbethoxy-4,6-dichloro-1-(tert-butyloxycarbonyl)-indole Mix 3-[(p-trifluoromethylphenacyl)amino]-2-carbethoxy-4,6-dichloroindole (1.18 g, 2.6 mmol), di-tert-butyl dicarbonate (610 mg, 2.8 mmol), tetrahydrofuran (25 mL), dimethylaminopyridine (42 mg, 0.3 mmol) and stir at room temperture for 15 minutes. Dilute with ethyl acetate (100 mL), wash with water saturated sodium chloride, dry over magnesium sulfate, filter and concentrate in vacuo. Recrystallize the residue from hot hexane containing some diethyl ether to yield the title compound (1.1 g,77%) as colorless crystals; mp 159°–160° C.

Anal. Calcd for $C_{24}H_{21}Cl_2F_3N_2O_5$: C, 52.86; H, 3.88; N, 5.14; Found: C, 52.89; H, 4.11; N, 5.39.

Scheme I, step e:
3-[(p-trifluoromethylphenacyl)methylamino]-2-carbethoxy-4,6-dichloro-1-(tert-butyloxycarbonyl)-indole Suspend sodium hydride (88 mg of a 60% dispersion, 2.2 mmol) in anhydrous tetrahydrofuran/dimethylformamide (5 mL/2:1) and cool to 0° C. under a nitrogen atmosphere. Add 3-[(p-trifluoromethylphenacyl)amino]-2-carbethoxy-4,6-dichloro-1-(tert-butyloxycarbonyl)-indole (1.1 g, 2.0 mmol) in tetrahydrofuran/dimethylformamide (20 mL/2:1) dropwise to the suspension. Stir at 0° C. for 30 minutes. Add methyl iodide (0.137 mL, 2.2 mmol) and stir for 30 minutes at 0° C. Warm the reaction to room temperature and after 4 hours quench with water. Extract with ethyl acetate, wash with saturated sodium chloride, dry over magnesium sulfate, filter and concentrate in vacuo to yield the title compound.

Scheme I, step f:
3-[(p-trifluoromethylphenacyl)methylamino]-2-carbethoxy-4,6-dichloroindole Dissolve 3-[(p-trifluoromethylphenacyl)methylamino]-2-carbethoxy-4,6-dichloro-1-(tert-butyloxycarbonyl)-indole from above in methylene chloride (5 mL). Add trifluoracetic acid (3 mL) and stir for 5 hours. Concentrate the reaction in vacuo, dilute with ethyl acetate (100 mL), wash with saturated sodium carbonate, dry over magnesium sulfate, filter and concentrate in vacuo. Recrystallize the residue from ethyl acetate/hexane to yield the title compound (820 mg).

Example 28m

Preparation of 3-[(p-trifluoromethylphenacyl)methylamino]-2-carbethoxy-4,6-dichloroindole

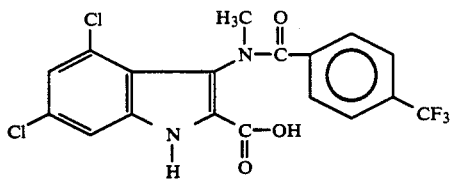

Mix 3-[(p-trifluoromethylphenacyl)methylamino]-2-carbethoxy-4,6-dichloroindole (750 mg, 1.7 mmol), lithium hydroxide (210 mg, 5 mmol), tetrahydrofuran (10 mL) and water (10 mL). Stir for 24 hours at room temperature. Dilute with ethyl acetate (40 mL). Acidify while stirring and separate the layers. Dry the organic phase over magnesium sulfate, filter and concentrate in vacuo. Recrystallize the residue (ethyl acetate/hexane) to yield the title compound as a white powder (590 mg, 81%); mp 232°–234° C.

Anal. Calcd for $C_{18}H_{11}Cl_2F_3N_2O_3$: C, 50.14; H, 2.57; N, 6.50; Found: C, 49.88; H, 2.61; N, 6.48.

Example 28n

Preparation of 3-[(p-chlorophenacyl)amino]-2-carbethoxy-4,6-dichloroindole

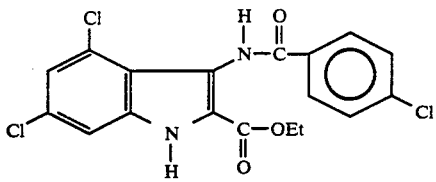

Dissolve 3-amino-2-carbethoxy-4,6-dichloroindole (2.2 g, 8 mmol) in methylene chloride (70 mL) and add triethylamine (1.16 mL, 8 mmol) followed by p-chlorobenzoyl chloride (0.976 mL, 8 mmol). Stir the reaction 48 hours at room temperature. Dilute the reaction with ethyl acetate (300 mL), wash with water (100 mL), dry the organic phase over magnesium sulfate, filter and concentrate in vacuo. Recrystallize the residue from ethyl acetate/hexane to yield the title compound as a fluffy solid (2.7 g, 79%).

Example 28p

Preparation of 3-[(p-chlorophenacyl)methylamino]-2-carbethoxy-4,6-dichloroindole

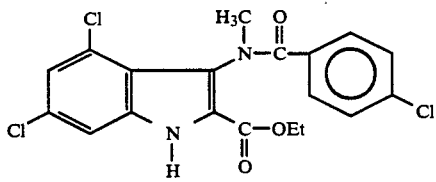

Scheme I, step d₂:
3-[(p-chlorophenacyl)amino]-2-carbethoxy-4,6-dichloro-1-(tert-butyloxycarbonyl)-indole Mix 3-[(p-chlorophenacyl)amino]-2-carbethoxy-4,6-dichloroindole (2 g, 4.8 mmol), di-tert-butyl dicarbonate (1 g, 4.8 mmol), tetrahydrofuran (90 mL), dimethylaminopyridine (42 mg, 0.3 mmol) and stir at room temperture for 1 hour. Dilute with ethyl acetate (100 mL), wash with water, saturated sodium chloride, dry orver magnesium sulfate, filter and concentrate in vacuo. Recrystallize the residue from ethyl acetate/hexane to yield the title compound (2.3 g, 94%).

Scheme I, step e:
3-[(p-chlorophenacyl)methylamino]-2-carbethoxy-4,6-dichloro-1-(tert-butyloxycarbonyl)-indole Suspend sodium hydride (160 mg of a 60% dispersion, 4 mmol) in anhydrous tetrahydrofuran/dimethylformamide (3 mL/2:1) and cool to 0° C. under a nitrogen atmosphere. Add 3-[(p-chlorophenacyl)amino]-2-carbethoxy-4,6-dichloro-1-(tert-butyloxycarbonyl)-indole (2 g, 3.9 mmol) in tetrahydrofuran/dimethylformamide (10 mL/2:1) dropwise to the suspension. Stir at 0° C. for 30 minutes. Add methyl iodide (0.137 mL, 2.2 mmol) and stir for 30 minutes at 0° C. Warm the reaction to room temperature and after 4 hours quench with water (20 mL). Extract with ethyl acetate (20 mL), wash with saturated sodium chloride, dry over magnesium sulfate, filter and concentrate in vacuo to yield the title compound.

Scheme I, step f:
3-[(p-chlorophenacyl)methylamino]-2-carbethoxy-4,6-dichloroindole Dissolve 3-[(p-chlorophenacyl)methylamino]-2-carbethoxy-4,6-dichloro-1-(tert-butyloxycarbonyl)-indole from above in methylene chloride (15 mL). Add trifluoroacetic acid (5 mL) and stir for 5 hours. Concentrate the reaction in vacuo, dilute with ethyl acetate (100 mL), wash with saturated sodium carbonate, dry over magnesium sulfate, filter and concentrate in vacuo. Recrystallize the residue from ethyl acetate/hexane to yield the title compound (1.3 g).

Example 28Q

Preparation of
3-[(p-chlorophenacyl)methylamino]-2-carboxy-4,6-dichloroindole

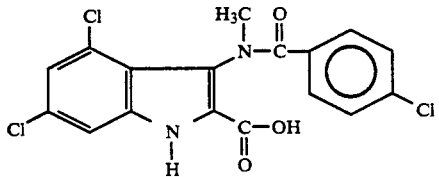

Mix 3-[(p-chlorophenacyl)methylamino]-2-carbethoxy-4,6-dichloroindole (1.3 g, 3.1 mmol), excess lithium hydroxide, tetrahydrofuran and water and stir overnight. Dilute with ethyl acetate and separate the layers. Dry the organic phase over magnesium sulfate, filter and concentrate in vacuo to yield the title compound; mp 279°-283° C.

Anal. Calcd for $C_{17}H_{11}Cl_3N_2O_3$: C, 51.35; H, 2.79; N, 7.04; Found: C, 51.30; H, 2.81; N, 7.00.

EXAMPLE 29

Preparation of
3-[(Phenylsulfonyl)amino]-2-carbethoxy-4,6-dichloroindole

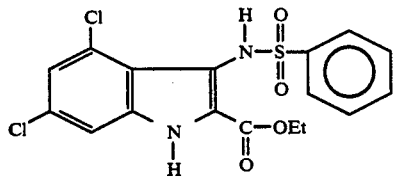

Mix 3-amino-2-carbethoxy-4,6-dichloroindole (3.31 g, and anhydrous pyridine (50 mL). Add, by dropwise addition, phenylsulfonyl chloride (2.35 g, 13.33 mmol). Stir for 48 hours at room temperature. Pour into 1N hydrochloric acid (500 mL), extract with ethyl acetate and dry (MgSO4). Evaporate the solvent in vacuo and recrystallize (ethyl acetate/hexane) to give the title compound (3.15 g, 63%); mp 245°-7° C.

EXAMPLE 30

Preparation of
3-[(Phenylsulfonyl)amino]-2-carboxy-4,6-dichloroindole

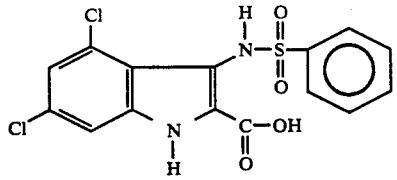

Mix 3-[(phenylsulfonyl)amino]-2-carbethoxy-4,6-dichloroindole (0.35 g, 0.847 mmol), tetrahydrofuran (10 mL) and water (7 mL). Add lithium hydroxide monohydrate (0.11 g, 2.54 mmol) and stir at room temperature overnight. Warm at 65° C. for 5 hours, pour into water and acidify to pH 1 with 1N hydrochloric acid. Extract into ethyl acetate, dry (MgSO4) and evaporate the solvent in vacuo. Recrystallize (ethyl acetate/hexane) to give the title compound (0.2 g, 61%); mp 229°-35° C. (dec).

EXAMPLE 31

Preparation of
3-[(Phenylsulfonyl)methylamino]-2-carbethoxy-4,6-dichloroindole

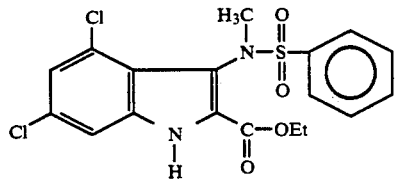

Scheme I, step d2:
3-[(Phenylsulfonyl)amino]-2-carbethoxy-4,6-dichloro-tert-butyloxycarbonyl-indole Dissolve 3-[(phenylsulfonyl)amino]-2-carbethoxy-4,6-dichloroindole (5.0 g, 12.10 mmol) in anhydrous tetrahydrofuran (200ml) and add di-tert-butyldicarbonate (2.91 g, 13.31 mmol), followed by dimethylaminopyridine (0.15 g, 1.21 mmol). Stir at room temperature for 24 hours, pour into 1N hydrochloric acid (200 mL) and extract into ethyl acetate. Wash with saturated sodium chloride, dry (MgSO4) and evaporate the solvent in vacuo to give 6.34 g crude product. Recrystallize (ethyl acetate/hexane) to give the title compound.

Scheme I, step e:
3-[(Phenylsulfonyl)methylamino]-2-carbethoxy-4,6-dichloro-tert-butyloxycarbonyl-indole Mix 3-[(phenylsulfonyl)amino]-2-carbethoxy-4,6-dichloro-tert-butyloxycarbonyl-indole (0.77 g, 1.5 mmol), methanol (52.9 mg, 1.65 mmol), triphenylphosphine (434 mg, 1.65 mmol) and anhydrous tetrahydrofuran (10 mL). Add, by dropwise addition, a solution of diethyl azodicarboxylate (288 mg, 1.65 mmol) in anhydrous tetrahydrofuran (10 mL). Stir at room temperature for 5 hours. Evaporate the solvent in vacuo and purify by flash chromatography (10% ethyl acetate/hexane) to give the title compound (490 mg, 62%).

Scheme I, step f:
3-[(Phenylsulfonyl)methylamino]-2-carbethoxy-4,6-dichloroindole Dissolve 3-[(phenylsulfonyl)methylamino]-2-carbethoxy-4,6-dichloro-tert-butyloxycarbonyl-indole (400 mg, 0.758 mmol) in methylene chloride (15 mL). Add, by dropwise addition, trifluoroacetic acid (15 mL) and stir at room temperature for 3 hours. Evaporate the solvent in vacuo and treat the resulting residue with saturated sodium hydrogen carbonate. Extact into methylene chloride and dry (MgSO₄). Recrystallize (ethyl acetate/hexane) to give the title compound (70 mg, 22%); mp 244°–45° C.

EXAMPLE 32

Preparation of
3-[(Phenylsulfonyl)methylamino]-2-carboxy-4,6-dichloroindole

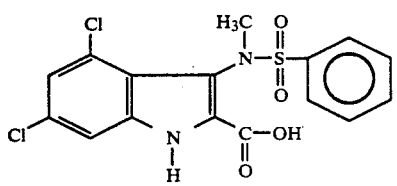

Mix 3-[(phenylsulfonyl)methylamino]-2-carbethoxy-4,6-dichloroindole (185 mg, 0.433 mmol), tetrahydrofuran (25 mL) and water (25 mL). Add lithium hydroxide monohydrate (2.6 mmol) and stir at room temperature for 3 days, then at reflux for 5 hours. Pour into 1N hydrochloric acid (200 mL) and extract into ethyl acetate. Dry (MgSO₄) and evaporate the solvent in vacuo. Recrystallize (ethyl acetate/hexane) to give the title compound (122 mg, 71%); mp 286°–90° C.

EXAMPLE 33

Preparation of
3-[(Methyloxalylate)amino]-2-carbethoxy-4,6-dichloroindole

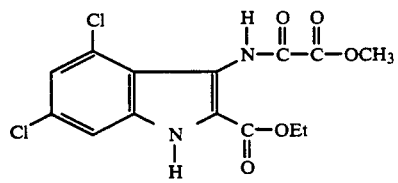

Mix 3-amino-2-carbethoxy-4,6-dichloroindole (3.8 g, 13.91 mmol), triethylamine (1.55 g, 15.3 mmol) and methylene chloride (250 mL). Add methyl oxalylchloride (1.88 g, 15.30 mmol) at stir at room temperature for 3.5 hours. Pour into saturated sodium hydrogen carbonate and separate the organic phase. Wash with saturated sodium chloride, dry (MgSO₄) and evaporate the solvent in vacuo to give a tan solid. Recrystallize (ethyl acetate/hexane) to give the title compound (3.47 g, 69%); mp 192°–3° C.

EXAMPLE 34

Preparation of
3-[(Oxalyl)amino]-2-carboxy-4,6-dichloroindole

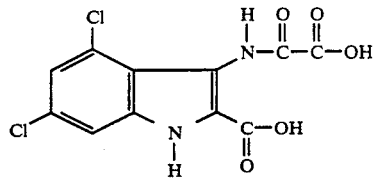

Dissolve 3-[(methyloxalylate)amino]-2-carbethoxy-4,6-dichloroindole (180 mg, 0.5 mmol) in tetrahydrofuran (2.5 mL) and water (2.5 mL). Add lithium hydroxide monohydrate (1.5 mmol) and stir overnight at room temperature. Dilute with water and wash with ethyl acetate. Acidify with 6N hydrochloric acid and extract with ethyl acetate. Dry (MgSO₄) and evaporate the solvent in vacuo. Recrystallize (ethyl acetate/hexane) to give the title compound (70 mg, 45%).

EXAMPLE 35

Preparation of
3-[(Methyloxalylate)benzylamino]-2-carbethoxy-4,6-dichloroindole

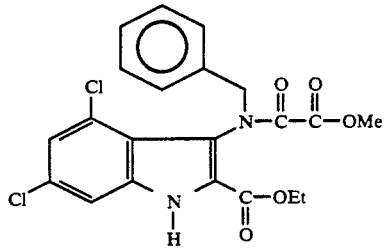

Scheme I, step d2:
3-[(Methyloxalylate)amino]-2-carbethoxy-4,6-dichloro-1-tert-butyloxycarbonyl-indole Dissolve 3-[(methyloxalylate)amino]-2-carbethoxy-4,6-dichloroindole (2.04 g, 5.70 mmol) in tetrahydrofuran (40 mL) and add di-tert-butyl dicarbonate (1.37 g, 6.27 mmol) and dimethylaminopyridine (catalytic). Stir at room temperature for 24 hours and evaporate the solvent in vacuo. Purify by flash chromatography (2:1 hexane/ethyl acetate) to give 1.51 g crude product. Recrystallize (ethyl acetate/hexane) to give the title compound (1.28 g, 49%).

Scheme I, step e:
3-[(Methyloxalylate)benzylamino]-2-carbethoxy-4,6-dichloro-1-tert-butyloxycarbonyl-indole Suspend sodium hydride (47.9 mg of a 60% dispersion, 1.20 mmol) in dimethylformamide (10 mL), cool to 0° C. and place under an inert atmosphere. Add a solution of 3-[(methyloxalylate)amino]-2-carbethoxy-4,6-dichloro-1-tert-butyloxycarbonyl-indole (500 mg, 1.09 mmol) in dimethylformamide (15 mL). Stir for 20 minutes, remove the ice bath and stir for an additional 15 minutes. Add benzyl bromide (205 mg, 1.20 mmol) and stir for 3 hours. Pour onto 1N hydrochloric acid and extract with ethyl ether. Dry and evaporate the solvent in vacuo to give a white solid. Recrystallize (ethyl acetate/hexane) to give the title compound (426 mg, 72%).

Scheme I, step f:
3-[(Methyloxalylate)benzylamino]-2-carbethoxy-4,6-dichloroindole Dissolve 3-[(methyloxalylate)benzylamino]-2-carbethoxy-4,6-dichloro-1-tert-butyloxycarbonyl-indole (351 mg, 0.586 mmol) in methylene chloride (15 mL) and add trifluroracetic acid (15 mL). Stir for 24 hours and pour into saturated sodium hydrogen carbonate (100 mL). Extract into methylene chloride, wash with water, dry (MgSO$_4$) and evaporate the solvent in vacuo. Recrystallize (ethyl acetate/hexane) to give the title compound as white crystals (70 mg, 27%); mp 183°-85° C.

EXAMPLE 36

Preparation of
3-[(Oxalyl)benzylamino]-2-carboxy-4,6-dichloroindole

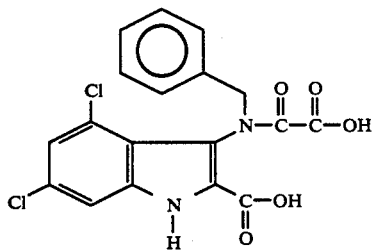

Mix 3-[(methyloxalylate)benzylamino]-2-carbethoxy 4,6-dichloroindole (180 mg, 0.401 mmol), tetrahydrofuran (12.5 mL) and water (12.5 mL). Add lithium hydroxide monohydrate (67 mg, 1.6 mmol) and stir at room temperature for 48 hours. Pour into 1N hydrochloric acid (100 mL) and extract with ethyl acetate. Dry (MgSO$_4$) and evaporate the solvent in vacuo. Recrystallize (ethyl acetate/hexane) to give the title compound as a white solid (126 mg, 77%); mp 228°-32° C. (dec).

EXAMPLE 37

Preparation of
3-[(Methyloxalylate)methylamino]-2-carbethoxy-4,6-dichloroindole

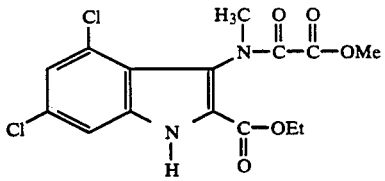

Scheme I, step e:
3-[(Methyloxalylate)methylamino]-2-carbethoxy-4,6-dichloro-1-tert-butyloxycarbonyl-indole Suspend sodium hydride (47.96 mg of a 60% dispersion, 1.20 mmol) in dimethylformamide (20 mL), cool to 0° C. and place under nitrogen atmosphere. Add, by dropwise addition, a solution of 3-[(methyloxalylate)amino]-2-carbethoxy-4,6-dichloro-tert-butyloxycarbonyl-indole (500 mg, 1.09 mmol) in dimethylformamide (30 mL). Allow to warm to room temperature and stir for 30 minutes. Add methyl iodide (170 mg) and stir overnight. Pour onto 1N hydrochloric acid and extract with ethyl ether. Dry and evaporate the solvent in vacuo. Recrystallize (ethyl acetate/hexane) to give the title compound.

Scheme I, step f:
3-[(Methyloxalylate)methylamino]-2-carbethoxy-4,6-dichloroindole Dissolve 3-[(methyloxalylate)methylamino]-2-carbethoxy-4,6-dichloro-1-tert-butyloxycarbonyl-indole (430 mg, 0.909 mmol) in methylene chloride (15 mL). Add trifluoroacetic acid (20 mL) and stir for 24 hours. Evaporate the solvent in vacuo and treat the resulting residue with saturated sodium hydrogen carbonate. Extact into methylene chloride and dry (MgSO$_4$). Evaporate the solvent in vacuo and recrystallize (ethyl acetate/hexane) to give the title compound (221 mg, 65%).

EXAMPLE 38

Preparation of
3-[(Oxalyl)methylamino]-2-carboxy-4,6-dichloroindole

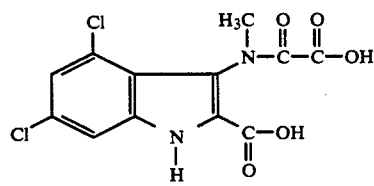

Mix 3-[(methyloxalylate)methylamino]-2-carbethoxy-4,6-dichloroindole (156 mg, 0.418 mmol) in tetrahydrofuran (25 mL) and water (25 mL). Add lithium hydroxide monohydrate (88 mg, 2.09 mmol) and stir for 24 hours. Pour into 1N hydrochloride acid and extract into ethyl acetate. Wash with water, dry (MgSO$_4$) and evaporate the solvent in vacuo. Recrystallize (ethyl acetate/hexane) to give the title compound as a white solid (114 mg, 83%); mp 230°-34° C. (dec).

EXAMPLE 39

Preparation of
3-[(4-Nitrophenacyl)amino]-2-carbethoxy-4,6-dichloroindole

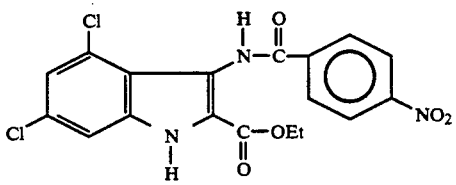

Dissolve 3-amino-2-carbethoxy-4,6-dichloroindole (10 g, 36.6 mmol) in anhydrous pyridine (100 mL). Add 4-nitrobenzoyl chloride (7.47 g, 40.27 mmol) and stir for 5 hours. Pour into 1N hydrochloric acid (500 mL) and extract into ethyl acetate. Evaporate the solvent in vacuo and dry at 70° C. under vacuum to give the title compound (15.75 g, 100%); mp 283°-86° c.

EXAMPLE 40

Preparation of
3-[(4-Nitrophenacyl)amino]-2-carboxy-4,6-dichloroindole

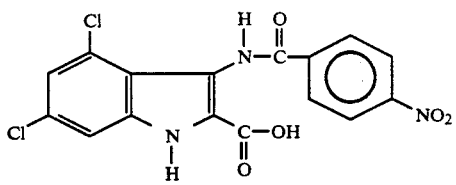

Mix 3-[(4-nitrophenacyl)amino]-2-carbethoxy-4,6-dichloroindole (161 mg, 0.381 mmol), tetrahydrofuan (20 ml) and water (20 mL). Add lithium hydroxide monohydrate (64 mg, 1.52 mmol) and stir overnight. Heat at reflux for 4 hours, cool to room temperature and pour onto 1N hydrochloric acid (100 mL). Collect the resulting solid by filtration and air dry to give the title compound (148 mg, 99%); mp 270°–72° C.

EXAMPLE 41

Preparation of
3-[(4-Aminophenacyl)amino]-2-carbethoxy-4,6-dichloroindole

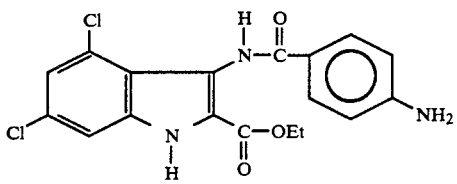

Dissolve 3-[(4-nitrophenacyl)amino]-2-carbethoxy-4,6-dichloroindole (0.5 g, 1.184 mmol) in ethanol (20 mL) and tin (II) chloride monohydrate (1.06 g, 7.1 mmol). Heat to 70° C. overnight. Pour into ethyl acetate/water (200 mL) and add solid sodium hydrogen carbonate to obtain pH 7. Filter and evaporate the solvent in vacuo to give the title compound as a pale yellow oil (0.477, 100%).

Example 41a

Preparation of
3-[(phenacyl)amino]-2-carbethoxy-5,6-dichloroindole

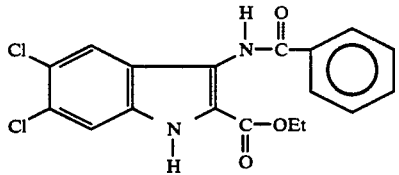

Scheme IV, step a, Preparation of starting material:
3-Nitro-2-carbethoxy-5,6-dichloroindole Dissolve 3,4-dichlorophenylhydrazine hydrochloride (300 g) in anhydrous ethanol (2L). Add ethyl pyruvate (153.6 mL) and concentrated sulfuric acid (25 mL). Sir at room temperature under a nitrogen atmosphere for 3 hours. Evaporate the solvent in vacuo, take up the residue in ethyl acetate/water and treat with saturated sodium hydrogen carbonate. Separate the aqueous phase and extract with ethyl acetate. Combine the organic phases, dry (MgSO$_4$) and evaporate the solvent in vacuo to give the 3,4-dichlorophenylhydrazone of ethyl pyruvate and as a solid. Both E and Z isomers are obtained.

Add polyphosphoric acid (2kg) to the 3,4-dichlorophenylhydrazone of ethyl pyruvate (100 g) and heat on a steam bath for 5 hours. Add a small amount of ice and pour onto ice to decompose the polyphosphoric acid. Extract the resulting suspension into ethyl acetate (3 × 1 L) and dry (MgSO$_4$). Evaporate the solvent in vacuo to give a light brown solid. Stir the solid with ethyl ether (1 L) for 1 hour and filter off 2-carboxyethyl-4,6-dichloroindole. Heat the filtrate with activated charcoal, filter through diatomaceous earth and evaporate the solvent in vacuo to give a second crop of 2-carboxyethyl-4,5-dichloroindole as a tan solid ( 89.4 g total, 95%).

Mix 2-carboxyethyl-5,6-dichloroindole (50 g) and acetic acid (1 L) and add, by dropwise addition, 90% (white fuming) nitric acid (250 mL). Apply a water bath as necessary to keep the temperature below 29° C. Stir for 10 minutes after all of the solid is dissolved and pour into ice (6L). Filter off the solid and wash with water. Dissolve the solid in ethyl acetate, treat with saturated sodium hydrogen carbonate solution, and separate the organic phase. Dry (MgSO$_4$), filter and evaporate the solvent in vacuo to give the crude product as a tan solid. Slurry the solid in a small amount of chloroform, filter and dry to give the title compound.

Scheme IV, step b:
3-Amino-2-carbethoxy-5,6-dichloroindole

Dissolve 3-nitro-2-carbethoxy-5,6-dichloroindole (38.1 g) in ethanol (1 L) and add tin (II) chloride dihydrate (163 g). Warm to between 65° and 75° C. for 4 to 5 hours. Cool to room temperature and pour into a mixture of ethyl acetate (3 L) and water (2 L). Add solid potassium carbonate and stir occasionally until the carbon dioxide evolution ceases. Filter throught diatomaceous earth and separate the organic phase of the filtrate. Dry (MgSO$_4$) and evaporate the solvent in vacuo to give the title compound.

Scheme I, step c:
3-[(phenacyl)amino]-2-carbethoxy-5,6-dichloroindole

Dissolve 3-amino-2-carbethoxy-5,6-dichloroindole (2.2 g, 8 mmol) in methylene chloride (70 mL) and add triethylamine (1.16 mL, 8 mmol) followed by benzoyl chloride (0.93 mL, 8 mmol). Stir the reaction 48 hours at room temperature. Dilute the reaction with ethyl acetate (300 mL), wash with water (100 mL), dry the organic phase over magnesium sulfate, filter and concentrate in vacuo. Recrystallize the residue from ethyl acetate/hexane to yield the title compound.

Example 41b

Preparation of
3-[(phenacyl)methylamino]-2-carbethoxy-5,6-dichloroindole

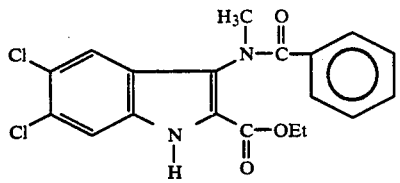

Scheme I, step d₂:
3-[(phenacyl)amino]-2-carbethoxy-5,6-dichloro-1-(tert-butyloxycarbonyl)-indole Mix 3-[(phenacyl)amino]-2-carbethoxy-5,6-dichloroindole (2 g, 4.8 mmol), di-tert-butyl dicarbonate (1 g, 4.8 mmol), tetrahydrofuran (90 mL), dimethylaminopyridine (42 mg, 0.3 mmol) and stir at room temperture for 1 hour. Dilute with ethyl acetate (100 mL), wash with water, saturated sodium chloride, dry orver magnesium sulfate, filter and concentrate in vacuo. Recrystallize the residue from ethyl acetate/hexane to yield the title compound.

Scheme I, step e:
3-[(phenacyl)methylamino]-2-carbethoxy-5,6-dichloro-1-(tert-butyloxycarbonyl)-indole Suspend sodium hydride (160 mg of a 60% dispersion, 4 mmol) in anhydrous tetrahydrofuran/dimethylformamide (3 mL/2:1) and cool to 0° C. under a nitrogen atmosphere. Add 3-[(phenacyl)amino]-2-carbethoxy-5,6-dichloro-1-(tert-butyloxycarbonyl)-indole (2 g, 3.9 mmol) in tetrahydrofuran/dimethylformamide (10 mL/2:1) dropwise to the suspension. Stir at 0° C. for 30 minutes. Add methyl iodide (0.137 mL, 2.2 mmol) and stir for 30 minutes at 0° C. Warm the reaction to room temperature and after 4 hours quench with water (20 mL). Extract with ethyl acetate (20 mL), wash with saturated sodium chloride, dry over magnesium sulfate, filter and concentrate in vacuo to yield the title compound.

Scheme I, step f:
3-[(phenacyl)methylamino]-2-carbethoxy-5,6-dichloroindole

Dissolve 3-[(phenacyl)methylamino]-2-carbethoxy-5,6-dichloro-1-(tert-butyloxycarbonyl)-indole from above in methylene chloride (15 mL). Add trifluoroacetic acid (5 mL) and stir for 5 hours. Concentrate the reaction in vacuo, dilute with ethyl acetate (100 mL), wash with saturated sodium carbonate, dry over magnesium sulfate, filter and concentrate in vacuo. Recrystallize the residue from ethyl acetate/hexane to yield the title compound.

Example 41c

Preparation of
3-[(phenacyl)methylamino]-2-carbethoxy-5,6-dichloroindole

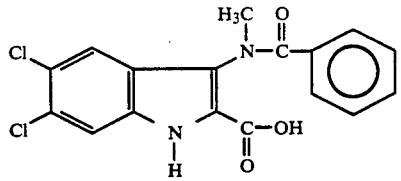

Mix 3-[(phenacyl)methylamino]-2-carbethoxy-5,6-dichloroindole (750 mg, 1.78 mmol), lithium hydroxide (210 mg, mmol), tetrahydrofuran (10 mL) and water (10 mL). Stir for 24 hours at room temperature. Dilute with ethyl acetate (40 mL). Acidify while stirring and separate the layers. Dry the organic phase over magnesium sulfate, filter and concentrate in vacuo. Recrystallize the residue (ethyl acetate/hexane) to yield the title compound.

EXAMPLE 41d

Preparation of
3-[(phenacyl)methylamino]-2-carbonylaminotetrazole-6-chloroindole

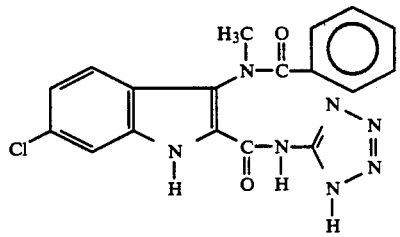

Scheme IV. Dissolve 3-[(phenacyl)methylamino]-2-carboxy-6-chloroindole (1 mmol) in toluene, add thionyl chloride (2 mL) and warm to 50° C. for 3 hours. After cooling, concentrate the reaction in vacuo and reconcentrate two more times from toluene. Dissolve the acid chloride in methylene chloride and treat with 5-aminotetrazole (1 mmol). Stir the reaction for 24 hours. Dilute the reaction with water, extract with ethyl acetate, dry the organic phase over magnesium sulfate, filter and concentrate to yield the title compound.

The compounds of Formulae Ia through Ic are excitatory amino acid antagonists. They antagonize the effects which excitatory amino acids have upon the NMDA receptor complex. They preferentially bind to the strychnine-insensitive glycine binding site associated with the NMDA receptor complex. They are useful in the treatment of a number of disease states.

The compounds exhibit anti-convulsant properties and are useful in the treatment of epilepsy. They are useful in the treatment of grand mal seizures, petit mal seizures, psychomotor seizures, autonomic seizures, etc. One method of demonstrating their anti-epileptic properties is by their ability to inhibit the seizures that are caused by the administration of quinolinic acid. This test can be conducted in the following manner.

One group containing ten mice are administered 0.01–100 μg of test compound intracerebroventricularly in a volume of 5 microliters of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of clonic-tonic seizures. The control group will have a statistically higher rate of clonic-tonic seizures than will the test group.

Another method of demonstrating the anti-epileptic properties of these compounds is by their ability to inhibit audiogenic convulsions in DBA/2 mice. This test can be conducted in the following manner. Typically one group of from 6–8 male DBA/2J audiogenic susceptible mice are administered from about 0.01 $\mu$g to about 100 $\mu$g of the test compound. The test compound is administered intracerebrally into the lateral ventricle of the brain. A second group of mice are administered an equal volume of saline control by the same route. Five minutes later the mice are placed individually in glass jars and are exposed to a sound stimulus of 110 decibels for 30 seconds. Each mouse is observed during the sound exposure for signs of seizure activity. The control group will have a statistically higher incidence of seizures than the group which receives the test compound.

The compounds of Formulae Ia through Ic are useful for preventing or minimizing the damage which nervous tissues contained within the CNS suffer upon exposure to either ischemic, hypoxic, or hypoglycemic conditions or as the result of physical trauma. Representative examples of such conditions include strokes or cerebrovascular accidents, hyperinsulinemia, cardiac arrest, physical trauma, drownings, suffocation, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds are also useful in the treatment of neurodegenerative diseases such as Huntington's disease, Alzheimer's disease, senile dementia, glutaric acidaemia type I, Parkinson's disease, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease, or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C. R., Distress vocalization in rat pups: a simple screening method for anxiolytic drugs. *J. Pharmacol. Methods,* 14:181-187 (1985) and Insel et al. Rat pup ultrasonic isolation calls: Possible mediation by the benzodiazepine receptor complex. *Pharmacol. Biochem. Behav.,* 24: 1263-1267 (1986).

The compounds also exhibit an analgesic effect and are useful in controlling pain. The compounds are also effective in the treatment of migraine.

In order to exhibit these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 50 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperioneally, or intrathecally).

Pharmaceutical compositions can be manufactured utilizing techniques known in the art. Typically an antagonistic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients.

Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The phrmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art.

As used in this application:

a) the term "patient" refers to warm blooded animals such as, for example, guinea pigs, mice, rats, cats, rabbits, dogs, monkeys, chimpanzees, and humans;

b) the term "treat" refers to the ability of the compounds to either relieve, alleviate, or slow the progression of the patient's disease or prophylactically prevent its occurence or the manifestation of its symptoms;

c) the term "neurodegeneration" refers to a progressive death and disappearance of a population of nerve cells occurring in a manner characteristic of a particular disease state and leading to brain damage.

The compounds of Formula I may also be admixed with any inert carrier and utilized in laboratory assays in order to determine the concentration of the compounds within the serum, urine, etc., of the patient as is known in the art.

Neurodegenerative diseases are typically associated with a loss of NMDA receptors. Thus, the compounds of Formulae Ia through Ic may be utilized in diagnostic procedures to aid physicians with the diagnosis of neurodegenerative diseases. The compounds may be labelled with imaging agents known in the art such as isotopic atoms and administered to a patient in order to determine whether the patient is exhibiting a decreased number of NMDA receptors and the rate at which that loss is occurring.

What is claimed is:

1. A compound of the formula:

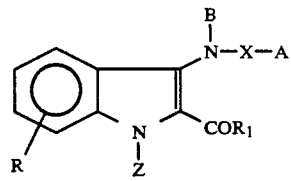

in which Z is represented by H, $C_1$-$C_4$ alkyl, phenyl, substituted phenyl, or a phenylalkyl substituent in which the phenyl ring may be optionally substituted; R is represented by hydrogen, halogen, $C_1$-$C_4$ alkyl, $C_1$-$C_4$ alkoxy, $CF_3$, $OCF_3$, OH, $NO_2$, or CN; B is represented by hydrogen, $C_1$-$C_4$ alkyl, optionally substituted phenylalkyl, or —$CH_2$—$COR_2$; X is represented by CO or $SO_2$; A is represented by:

in which L is represented by a substituent selected from the group consisting of hydrogen, halogen, $C_1$-$C_4$ alkyl, $C_1$-$C_4$ alkoxy, $CF_3$, $OCF_3$, OH, $NO_2$, $NH_2$, phenylalkyl, acetyloxy or CN; $R_1$, and $R_2$, are each independently represented by a substituent selected from the group consisting of —OH, —$OR_3$, —$NR_4R_5$, —$OCH_2OR_3$, and —O—$(CH_2)_m$—$NR_6R_7$, in which m is an integer from 1–4; $R_3$ is represented by $C_1$-$C_4$ alkyl, phenyl, substituted phenyl or a phenylalkyl substituent in which the phenyl ring may be optionally substituted; $R_4$ and $R_5$ are each independently represented by hydrogen or a $C_1$-$C_4$ alkyl ; $R_6$ and $R^7$ are each independently represented by hydrogen or a $C_1$-$C_4$ alkyl; the pharmaceutically acceptable salt thereof; with the following proviso's 1) that when R, Z, B, are hydrogen, $R_1$ is $OR_3$ in which $R_3$ is ethyl, and X is CO, then L is not hydrogen; 2) that when X is $SO_2$, R and B are hydrogen, and Z is methyl, then L is not para $NO_2$, para Methyl, or para chlorine; 3) that when X is $SO_2$, R and B are hydrogen, and Z is H, then L is not para Cl.

2. A compound according to claim 1 in which B is $C_1$-$C_4$ alkyl, optionally substituted phenylalkyl, or —$CH_2$—$COR_2$.

3. A compound according to claim 1 in which X is CO.

4. A compound according to claim 1 in which X is $SO_2$.

5. A compound according to claim 1 in which R is 4,6-, or 5,6-dichloro-.

6. A compound according to claim 1 in which R is 6-chloro-.

7. A compound according to claim 1 in which said compound is 3-[(2-acetoxyphenacyl)amino]-2-carbmethoxy-6-chloroindole.

8. A compound according to claim 1 in which said compound is 3-[(2-hydroxyphenacyl)amino]-2-carboxy-6-dichloroindole.

9. A compound according to claim 1 in which said compound is 3-[(phenacyl)amino]-2-carbmethoxy-6-chloroindole.

10. A compound according to claim 1 in which said compound is 3-[(phenacyl)amino]-2-carboxy-6-chloroindole.

11. A compound according to claim 1 in which said compound is 3-[(phenacyl)methylamino]-2-carbmethoxy-6-chloroindole.

12. A compound according to claim 1 in which said compound is 3-[(phenacyl)methylamino]-2-carboxy-6-chloroindole.

13. A compound according to claim 1 in which said compound is 3-[(m-fluorophenacyl)amino]-2-carbmethoxy-6-chloroindole.

14. A compound according to claim 1 in which said compound is 3-[(m-fluorophenacyl)methylamino]-2-carbmethoxy-6-chloroindole.

15. A compound according to claim 1 in which said compound is 3-[(m-fluorophenacyl)methylamino]-2-carboxy-6-chloroindole.

16. A compound according to claim 1 in which said compound is 3-[(p-fluorophenacyl)amino]-2-carbmethoxy-6-chloroindole.

17. A compound according to claim 1 in which said compound is 3-[(p-fluorophenacyl)methylamino]-2-carbmethoxy-6-chloroindole.

18. A compound according to claim 1 in which said compound is 3-[(p-fluorophenacyl)methylamino]-2-carboxy-6-chloroindole.

19. A compound according to claim 1 in which said compound is 3-[(3,4-difluorophenacyl)amino]-2-carbmethoxy-6-chloroindole.

20. A compound according to claim 1 in which said compound is 3-[(3,4-difluorophenacyl)methylamino]-2-carbmethoxy-6-chloroindole.

21. A compound according to claim 1 in which said compound is 3-[(3,4-difluorophenacyl)methylamino]-2-carboxy-6-chloroindole.

22. A compound according to claim 1 in which said compound is 3-[(phenacyl)methylamino]-2-carboxy-6-fluoroindole.

23. A compound according to claim 1 in which said compound is 3-[(phenyl)methylamino]-2-carboxy-6-trifluoromethylindole.

24. A compound according to claim 1 in which said compound is 3-[(phenacyl)amino]-2-carboxy-6-nitroindole.

25. A compound according to claim 1 in which said compound is 3-[(phenacyl)amino]-2-[(2-dimethylamino)-carbethoxy]-6-chloroindole.

26. A compound according to claim 1 in which said compound is 3-[(phenacyl)amino]-2-carbethoxy-4,6-dichloroindole.

27. A compound according to claim 1 in which said compound is 3-[(phenacyl)amino]-2-carboxy-4,6-dichloroindole.

28. A compound according to claim 1 in which said compound is 3-[(phenacyl)methylamino]-2-carbethoxy-4,6-dichloroindole.

29. A compound according to claim 1 in which said compound is 3-[(phenacyl)methylamino]-2-carboxy-4,6-dichloroindole.

30. A compound according to claim 1 in which said compound is 3-[(phenacyl)methylamino]-2-sodium-carboxylate-4,6-dichloroindole.

31. A compound according to claim 1 in which said compound is 3-[(phenacyl)methylamino]-2-[(2-dimethylamino)-carbethoxy]-4,6-dichloroindole.

32. A compound according to claim 1 in which said compound is 3-[(phenacyl)ethylamino]-2-carbethoxy-4,6-dichloroindole.

33. A compound according to claim 1 in which said compound is 3-[(phenyl)ethylamino]-2-carboxy-4,6-dichloroindole.

34. A compound according to claim 1 in which said compound is 3-[(phenacyl)benzylamino]-2-carbethoxy-4,6-dichloroindole.

35. A compound according to claim 1 in which said compound is 3-[(phenacyl)benzylamino]-2carboxy-4,6-dichloroindole.

36. A compound according to claim 1 in which said compound is 3-[(phenacyl)carbethoxymethyl-amino-]-2-carbethoxy-4,6-dichloroindole.

37. A compound according to claim 1 in which said compound is 3-[(phenacyl)carboxymethyl-amino-]-2-carboxy-4,6-dichloroindole.

38. A compound according to claim 1 in which said compound is 3-[(2-benzylphenacyl)amino]-2-carbethoxy-4,6-dichloroindole.

39. A compound according to claim 1 in which said compound is 3-[(2-benzylphenacyl)amino]-2-carboxy-4,6-dichloroindole.

40. A compound according to claim 1 in which said compound is 3-[(2-benzylphenacyl)methylamino]-2-carbethoxy-4,6-dichloroindole.

41. A compound according to claim 1 in which said compound is 3-[(2-benzylphenacyl)methylamino]-2-carboxy-4,6-dichloroindole.

42. A compound according to claim 1 in which said compound is 3-[(p-fluorophenacyl)amino]-2-carbethoxy-4,6-dichloroindole.

43. A compound according to claim 1 in which said compound is 3-[(p-fluorophenacyl)amino]-2-carboxy-4,6-dichloroindole.

44. A compound according to claim 1 in which said compound is 3-[(p-fluorophenacyl)methylamino]-2-carbethoxy-4,6-dichloroindole.

45. A compound according to claim 1 in which said compound is 3-[(p-fluorophenacyl)methylamino]-2-carboxy-4,6-dichloroindole.

46. A compound according to claim 1 in which said compound is 3-[(o-fluorophenacyl)amino]-2-carbethoxy-4,6-dichloroindole.

47. A compound according to claim 1 in which said compound is 3-[(o-fluorophenacyl)methylamino]-2-carbethoxy-4,6-dichloroindole.

48. A compound according to claim 1 in which said compound is 3-[(o-fluorophenacyl)methylamino]-2-carboxy-4,6-dichloroindole.

49. A compound according to claim 1 in which said compound is 3-[(m-fluorophenacyl)amino-]-2-carbethoxy-4,6-dichloroindole.

50. A compound according to claim 1 in which said compound is 3-[(m-fluorophenacyl)methylamino]-2-carbethoxy-4,6-dichloroindole.

51. A compound according to claim 1 in which said compound is 3-[(m-fluorophenacyl)methylamino]-2-carboxy-4,6-dichloroindole.

52. A compound according to claim 1 in which said compound is 3-[(p-trifluoromethylphenacyl)amino]-2-carbethoxy-4,6-dichloroindole.

53. A compound according to claim 1 in which said compound is 3-[(p-trifluoromethylphenacyl)methylamino]-2-carbethoxy-4,6-dichloroindole.

54. A compound according to claim 1 in which said compound is 3-[(p-trifluoromethylphenacyl)methylamino]-2-carbethoxy-4,6-dichloroindole.

55. A compound according to claim 1 in which said compound is 3-[(p-chlorophenacyl)amino]-2-carbethoxy-4,6-dichloroindole.

56. A compound according to claim 1 in which said compound is 3-[(p-chlorophenacyl)methylamino]-2-carbethoxy-4,6-dichloroindole.

57. A compound according to claim 1 in which said compound is 3-[(p-chlorophenacyl)methylamino]-2-carboxy-4,6-dichloroindole.

58. A compound according to claim 1 in which said compound is 3-[(phenylsulfonyl)amino]-2-carbethoxy-4,6-dichloroindole.

59. A compound according to claim 1 in which said compound is 3-[(phenylsulfonyl)amino]-2-carboxy-4,6-dichloroindole.

60. A compound according to claim 1 in which said compound is 3-[(phenylsulfonyl)methylamino]-2-carbethoxy-4,6-dichloroindole.

61. A compound according to claim 1 in which said compound is 3-[(phenylsulfonyl)methylamino]-2-carboxy-4,6-dichloroindole.

62. A compound according to claim 1 in which said compound is 3-[(4-nitrophenacyl)amino]-2-carbethoxy-4,6-dichloroindole.

63. A compound according to claim 1 in which said compound is 3-[(4-nitrophenacyl)amino]-2-carboxy-4,6-dichloroindole.

64. A compound according to claim 1 in which said compound is 3-[(4-aminophenacyl)amino]-2-carbethoxy-4,6-dichloroindole.

65. A compound according to claim 1 in which said compound is 3-[(phenacyl)amino]-2-carbethoxy-5,6-dichloroindole.

66. A compound according to claim 1 in which said compound is 3-[(phenacyl)methylamino]-2-carbethoxy-5,6-dichloroindole.

67. A compound according to claim 1 in which said compound is 3-[(phenacyl)methylamino]-2-carbethoxy-5,6-dichloroindole.

68. A pharmaceutical composition comprising an effective amount of a compound according to claim 1 in admixture with a pharmaceutically acceptable carrier.

69. A method for antagonizing the effects of excitatory amino acids upon the NMDA receptor complex comprising administering to a patient in need thereof, an antagonistic amount of a compound according to claim 1.

70. A method for treatment of epilepsy comprising administering to a patient in need thereof an anti-epileptic amount of a compound according to claim 1.

71. A method for the treatment of neurodegenerative diseased comprising administering to a patient in need thereof an effective amount of a compound according to claim 1.

72. A method for preventing ischemic/hypoxic/hypoglycemic damage to cerebral tissue comprising administering to a patient in need thereof an effective amount of a compound according to claim 1.

73. A method for the treatment of anxiety comprising administering an anxiolytic amount of a compound according to claim 1.

74. A method for producing an analgesic effect comprising administering to a patient in need thereof an analgesic amount of a compound according to claim 1.

* * * * *